United States Patent
Yamaguchi et al.

(10) Patent No.: US 8,623,387 B2
(45) Date of Patent: Jan. 7, 2014

(54) EXTERNAL PREPARATION COMPOSITION COMPRISING FATTY ACID-BASED IONIC LIQUID AS ACTIVE INGREDIENT

(75) Inventors: Toshikazu Yamaguchi, Higashikagawa (JP); Kenta Kawai, Higashikagawa (JP); Katsuhiro Yamanaka, Higashikagawa (JP); Noboru Tatsumi, Higashikagawa (JP)

(73) Assignee: Medrx Co., Ltd., Kagawa (JP)

( * ) Notice: Subject to any disclaimer, the term of this patent is extended or adjusted under 35 U.S.C. 154(b) by 329 days.

(21) Appl. No.: 12/734,771

(22) PCT Filed: Nov. 20, 2008

(86) PCT No.: PCT/JP2008/003409
§ 371 (c)(1),
(2), (4) Date: May 21, 2010

(87) PCT Pub. No.: WO2009/066457
PCT Pub. Date: May 28, 2009

(65) Prior Publication Data
US 2010/0256174 A1    Oct. 7, 2010

(30) Foreign Application Priority Data

Nov. 22, 2007 (JP) ................................. 2007-303784
Aug. 6, 2008 (JP) ................................. 2008-202639

(51) Int. Cl.
*A61K 8/02* (2006.01)
*A61L 15/00* (2006.01)
*A61K 9/70* (2006.01)

(52) U.S. Cl.
USPC ........................... 424/401; 424/445; 424/449

(58) Field of Classification Search
USPC ......................... 424/401, 445, 449
See application file for complete search history.

(56) References Cited

U.S. PATENT DOCUMENTS

| | | | |
|---|---|---|---|
| 5,795,916 | A | 8/1998 | Sekine et al. |
| 2004/0001881 | A1 | 1/2004 | Seizer et al. |
| 2004/0101551 | A1 | 5/2004 | Seizer |
| 2004/0170672 | A1 | 9/2004 | Selzer |
| 2007/0196453 | A1 | 8/2007 | Zhang et al. |

FOREIGN PATENT DOCUMENTS

| | | | |
|---|---|---|---|
| GB | 1 518 683 | | 7/1978 |
| JP | 62-103015 | | 5/1987 |
| JP | 62-228027 | | 10/1987 |
| JP | 8-175972 | | 7/1996 |
| JP | 2007-008927 | * | 1/2007 |
| JP | 2008-184402 | | 8/2008 |
| WO | 96/04902 | | 2/1996 |

OTHER PUBLICATIONS

Supplementary European Search Report dated Dec. 16, 2010 in Application No. EP 08 85 2335.
Official Action issued Jul. 25, 2011 in corresponding Chinese Application No. 200880124974.3.
B. Lu, "New Dosage Forms and Techniques of the Drug", Peoples Medical Publishing House, First Edition, p. 364, Apr. 1998 (with English translation).
International Search Report issued Dec. 22, 2008 in International (PCT) Application No. PCT/JP2008/003409.
European Office Action issued Jul. 26, 2013 in corresponding European Patent Application No. 08 852 335.2.

* cited by examiner

*Primary Examiner* — Renee Claytor
(74) *Attorney, Agent, or Firm* — Wenderoth, Lind & Ponack, L.L.P.

(57) ABSTRACT

Disclosed is an external preparation composition having good transdermal absorbability. An external preparation composition having excellent transdermal absorbability can be produced by dissolving a medicinal substance or a salt thereof in a fatty acid-based ionic liquid to form a composite ionic composition of the medicinal substance. The external preparation composition can be used as a liquid preparation, an ointment, a cream, a plaster or the like, and enables to provide a preparation having excellent transdermal absorbability.

12 Claims, 3 Drawing Sheets

——— IR absorption of DEA x isostearic acid (equimolar)

- - - - - IR absorption of isostearic acid

- - - - IR absorption of diethanolamine

EXTERNAL PREPARATION COMPOSITION COMPRISING FATTY ACID-BASED IONIC LIQUID AS ACTIVE INGREDIENT This application is a U.S. national stage of International Application No. PCT/JP2008/003409 filed Nov. 20, 2008.

TECHNICAL FIELD

The present invention relates to an external preparation composition comprising a fatty acid-based ionic liquid as an essential ingredient. Particularly, the present invention relates to an external preparation composition containing a basic drug, an acidic drug, or a salt thereof. The present invention further relates to a transdermally absorbable external preparation containing the composition.

BACKGROUND ART

Various methods have been proposed so far for forming a transdermally absorbable preparation having the improved transdermal absorbability of a drug. First, ion pair formation has been attempted for improving the transdermal absorbability of a drug itself. Some of such attempts are described in, for example, Non-Patent Document 1 and Patent Document 1. Moreover, a patch containing a hydroxyethylpyrrolidine salt of diclofenac has currently been put on the US market as Flector (registered trademark) Patch (Patent Document 2).

Attempts to improve the transdermal absorbability of a drug by devising a solution for dissolving the drug have also been made as alternative methods for improving the transdermal absorbability of a drug. For example, a solvent system of animal or plant oil and fat, polyhydric alcohol, and water (Patent Document 3) or a solvent system of a carboxylic acid ester having 16 to 20 carbon atoms and an alcohol having 2 to 5 carbon atoms (Patent Document 4) has been shown to improve the transdermal absorption of a basic drug or the like.

Non-Patent Document 2 discloses that a lactic acid/ethanol/isopropyl myristate solvent system or a triethanolamine/ethanol/isopropyl myristate solvent system is a favorable solvent system for accelerating the transdermal absorption of a basic drug or an acidic drug.

However, the system of animal or plant fat and oil and polyhydric alcohol separates into two layers and hardly forms a uniform solution. On the other hand, in the ethanol/isopropyl myristate solvent system, which tends to form a uniform solvent system, the solvent composition is variable due to easily volatilized ethanol and hardly produces stable transdermal absorbability. In addition, Patent Document 5 (paragraph 0011) shows that a system of a lower alcohol and a fatty acid ester does not always produce the sufficient effect of accelerating absorption.

Thus, a solvent system that accelerates the transdermal absorption of a drug, has stable solvent composition, and suppresses the decomposition of the drug has been demanded as a solvent system for dissolving a drug to prepare an external preparation.

On the other hand, attempts have also been made to improve the transdermal absorbability of a drug by the addition of a transdermal absorption accelerator. For example, Patent Documents 6 and 8 have reported that the addition of an organic acid salt (e.g., sodium acetate) together with a basic drug improves the transdermal absorbability for a matrix-type patch. Moreover, in Patent Document 7, improvement in the transdermal absorbability for a matrix preparation has been attempted by the addition of an ammonium salt (e.g., diethylamine hydrochloride) together with an acidic drug.

However, more radical improvement in a solvent composition itself has been demanded for further improving the transdermal absorbability of a drug.

Patent Document 1: Japanese Patent Laid-Open No. 2005-82512
Patent Document 2: Japanese Patent No. 3526887
Patent Document 3: Japanese Patent Laid-Open No. 04-99716
Patent Document 4: Japanese Patent Laid-Open No. 06-40947
Patent Document 5: Japanese Patent Laid-Open No. 2007-8871
Patent Document 6: WO 00/61120
Patent Document 7: WO 01/005381
Patent Document 8: WO 01/007018
Non-Patent Document 1: Kazuyoshi Kubo and Tadanori Mayumi, Fragrance Journal, 1998-9, 71-78 (1998)
Non-Patent Document 2: Liang Fang et al., Biol. Pharm. Bull., 25, 1339-1344 (2002)

DISCLOSURE OF THE INVENTION

Problems to be Solved by the Invention

An object of the present invention is to overcome the status quo and to provide a solvent composition which stably dissolves a drug and improve the transdermal absorbability of the drug without change in the solvent composition over time.

Means for Solving the Problems

The present inventors conducted diligent studies and have consequently found that the use of an ionic liquid under nonaqueous conditions can enhance the stability of a drug in the solution, and the use of a fatty acid-based ionic liquid having 5 to 20 carbon atoms as a solvent can improve the transdermal absorbability of the drug by dissolving the drug or a salt thereof in the solvent to form a cluster ion composition. During the course of this process, the present inventors have found that the transdermal absorbability of acidic and basic drugs exhibit the following tendency in a fatty acid-based ionic liquid:

[Tendency of transdermal absorbability of acidic drug] isostearic acid>capric acid>oleic acid>levulinic acid
[Tendency of transdermal absorbability of basic drug] capric acid>oleic acid, levulinic acid>isostearic acid Moreover, when an acidic drug was used, no significant difference was found in transdermal absorbability among organic amine compounds used in the fatty acid-based ionic liquid. However, it was found that an organic amine compound having a basicity (pKa) higher than that of the drug had to be selected for improving the transdermal absorbability when a compound of hydrochloride was used as a basic drug. On the other hand, it was found that an organic amine compound having a basicity lower than that of the drug was preferably selected for a fatty acid salt of a basic drug.

The present inventors have further found that the drug or the drug can be transdermally absorbed more easily by dissolving a salt of the drug or the drug in an ionic liquid form (room temperature molten salt) in a fatty acid-based ionic liquid having 5 to 20 carbon atoms to form a cluster ion composition, which is then solvated in an appropriate organic solvent (mixed solvent of a proton-donor solvent and a proton-acceptor solvent). The present inventors have also found that the addition of a few % of fatty acid as a transdermal absorption accelerator further improve the transdermal absorption.

Moreover, the further finding of the present invention is that a fatty acid-based ionic liquid which is a salt of a fatty acid having 5 to 20 carbon atoms and an organic amine compound having 4 to 10 carbon atoms works like a surfactant for a transdermal absorption-accelerating solvent system (e.g., diethyl sebacate and propylene glycol), which tends to separate into two layers.

As a result, a drug-containing external preparation composition of the present invention is structurally a cluster ion composition comprising a drug and is further a solution containing a cluster ion composition solvated in an organic solvent. Moreover, even when a plurality of transdermal absorption-accelerating solvents, which tend to separate into two layers, are used as organic solvents, the external preparation composition of the present invention is a uniform solution by virtue of the effect of the fatty acid-based ionic liquid of the present invention. The present inventors found that the use of this uniform solution as a liquid preparation could further enhance the transdermal absorbability of the drug. Based on these findings, the present inventors completed the present invention.

Specifically, the present invention is summarized as follows:

(1) An external preparation composition comprising a drug or a salt thereof dissolved in a fatty acid-based ionic liquid having 5 to 20 carbon atoms.
(2) The external preparation composition according to (1), wherein the fatty acid-based ionic liquid is obtained from a fatty acid having 5 to 20 carbon atoms and an organic amine compound having 4 to 12 carbon atoms.
(3) The external preparation composition according to (1) or (2), wherein the drug is an acidic drug or a basic drug.
(4) The external preparation composition according to any of (1) to (3), wherein the external preparation composition is a nonaqueous external preparation composition.
(5) The external preparation composition according to any of (1) to (4), further comprising an organic solvent.
(6) The external preparation composition according to (5), wherein the external preparation composition is a liquid preparation.
(7) The external preparation composition according to (5), wherein the organic solvent comprises a mixed solvent of a proton-donor solvent and a proton-acceptor solvent.
(8) The external preparation composition according to any of (1) to (7), wherein the organic amine compound having 4 to 12 carbon atoms is an alkylamine compound having one or more hydroxyl group(s).
(9) The external preparation composition according to any of (1) to (8), wherein the organic amine compound having 4 to 12 carbon atoms is one or more selected from diethanolamine, triethanolamine, diisopropanolamine, and triisopropanolamine.
(10) The external preparation composition according to any of (1) to (9), wherein the salt of the drug is a salt in an ionic liquid form.
(11) The external preparation composition according to (10), wherein the salt in an ionic liquid form is a salt of an acidic drug and an organic amine compound having 4 to 12 carbon atoms, or a salt of a basic drug and a fatty acid having 5 to 20 carbon atoms.
(12) The external preparation composition according to any of (1) to (11), wherein the fatty acid having 5 to 20 carbon atoms is one or more selected from levulinic acid, capric acid, isostearic acid, and oleic acid.
(13) The external preparation composition according to any of (1) to (12), further comprising an organic acid.
(14) The external preparation composition according to any of (1) to (12), further comprising a pyrrolidone derivative.
(15) The external preparation composition according to any of (1) to (14), wherein the content of the fatty acid-based ionic liquid is 5 to 50 w/w %.
(16) The external preparation composition according to any of (1) to (14), wherein the content of the fatty acid-based ionic liquid is 5 to 25 w/w %.
(17) The external preparation composition according to any of (1) to (16), further comprising an organic acid or an organic base in up to 2-fold molar amount with respect to the amount of the drug or the salt thereof contained therein.
(18) The external preparation composition according to any of (1) to (17), wherein the acidic drug is NSAID.
(19) The external preparation composition according to (18), wherein the NSAID is selected from indomethacin, flurbiprofen, etodolac, ibuprofen, loxoprofen, ketoprofen, and diclofenac.
(20) The external preparation composition according to any of (1) to (17), wherein the basic drug is a local anesthetic, a muscle relaxant, an analgesic, or an opioid analgesic.
(21) The external preparation composition according to (20), wherein the local anesthetic is lidocaine.
(22) The external preparation composition according to (20), wherein the muscle relaxant is eperisone.
(23) The external preparation composition according to (20), wherein the analgesic is tramadol.
(24) The external preparation composition according to (20), wherein the opioid analgesic is morphine.
(25) The external preparation composition according to (7), wherein the proton-donor solvent is an alcohol solvent.
(26) The external preparation composition according to (7), wherein the proton-acceptor solvent is a fatty acid ester.
(27) The external preparation composition according to (25), wherein the alcohol solvent is selected from ethanol, isopropanol, and propylene glycol.
(28) The external preparation composition according to (26), wherein the fatty acid ester is isopropyl myristate or diethyl sebacate.
(29) The external preparation composition according to (13), wherein the organic acid is selected from acetic acid, oleic acid, and levulinic acid.
(30) The external preparation composition according to any of (1) to (29), wherein the content of the drug or the salt thereof is 0.5 to 30 w/w %.
(31) The external preparation composition according to any of (1) to (30), wherein the fatty acid-based ionic liquid is present in 0.3 to 20-fold molar amount with respect to the amount of the drug or the salt thereof.
(32) The external preparation composition according to any of (1) to (30), wherein the fatty acid-based ionic liquid is present in 3 to 20-fold molar amount with respect to the amount of the drug or the salt thereof.
(33) The external preparation composition according to (17), wherein the organic base is selected from diisopropanolamine, triisopropanolamine, diethanolamine, and triethanolamine.
(34) The external preparation composition according to (14), wherein the pyrrolidone derivative is N-methyl-2-pyrrolidone.
(35) A patch preparation comprising an external preparation composition according to any of (1) to (34) formulated with a styrene-isoprene-styrene copolymer as a patch base.

(36) An ointment preparation comprising an external preparation composition according to any of (1) to (34) formulated with Plastibase as an ointment base.

(37) A transdermal absorption accelerator for an acidic drug or a basic drug or a salt thereof, comprising, as an active ingredient, a fatty acid-based ionic liquid which comprises a fatty acid having 5 to 20 carbon atoms and an organic amine compound having 4 to 12 carbon atoms.

(38) The transdermal absorption accelerator according to (37), wherein the organic amine compound having 4 to 12 carbon atoms is alkylamine having one or more hydroxyl group(s).

(39) The transdermal absorption accelerator according to (37) or (38), wherein the fatty acid is isostearic acid.

(40) The transdermal absorption accelerator according to any of (37) to (39), wherein the organic amine compound is diisopropanolamine or triisopropanolamine.

(41) The transdermal absorption accelerator according to (37), which is intended to improve the transdermal absorption of an acidic drug or a salt thereof, wherein the fatty acid-based ionic liquid is an isostearic acid-based ionic liquid.

(42) The transdermal absorption accelerator according to (37), which is intended to improve the transdermal absorption of a basic drug or a salt thereof, wherein the fatty acid-based ionic liquid is a capric acid-based ionic liquid.

(43) An equimolar salt of isostearic acid and an organic amine compound having 4 to 12 carbon atoms.

(44) The equimolar salt according to (43), wherein the organic amine compound is an alkylamine compound having one or more hydroxyl group(s).

(45) The equimolar salt according to (43) or (44), wherein the organic amine compound is diisopropanolamine or diethanolamine.

Advantages of the Invention

A drug-containing external preparation composition comprising a fatty acid-based ionic liquid having 5 to 20 carbon atoms as an essential ingredient according to the present invention can stabilize the drug and improve its transdermal absorbability by the effect of addition of the fatty acid-based ionic liquid. The external preparation composition can further enhance the transdermal absorbability of the drug by forming therein a cluster ion composition, which is then supplemented with an additional fatty acid. Thus, the external preparation composition of the present invention can achieve excellent transdermal absorbability of a drug previously considered to have poor transdermal absorbability, by dissolving the drug in the fatty acid-based ionic liquid to fault a cluster ion composition, which is then controlled by solvation or the like.

From these viewpoints, the composition of the present invention can be applied to various external preparations such as liquid preparations, ointments, and patches. Furthermore, a matrix-type patch comprising the composition of the present invention formulated therein can also be prepared to provide a pharmaceutical product that exhibits favorable transdermal absorbability.

BEST MODE FOR CARRYING OUT THE INVENTION

—First Aspect of Present Invention—

Figure 1:
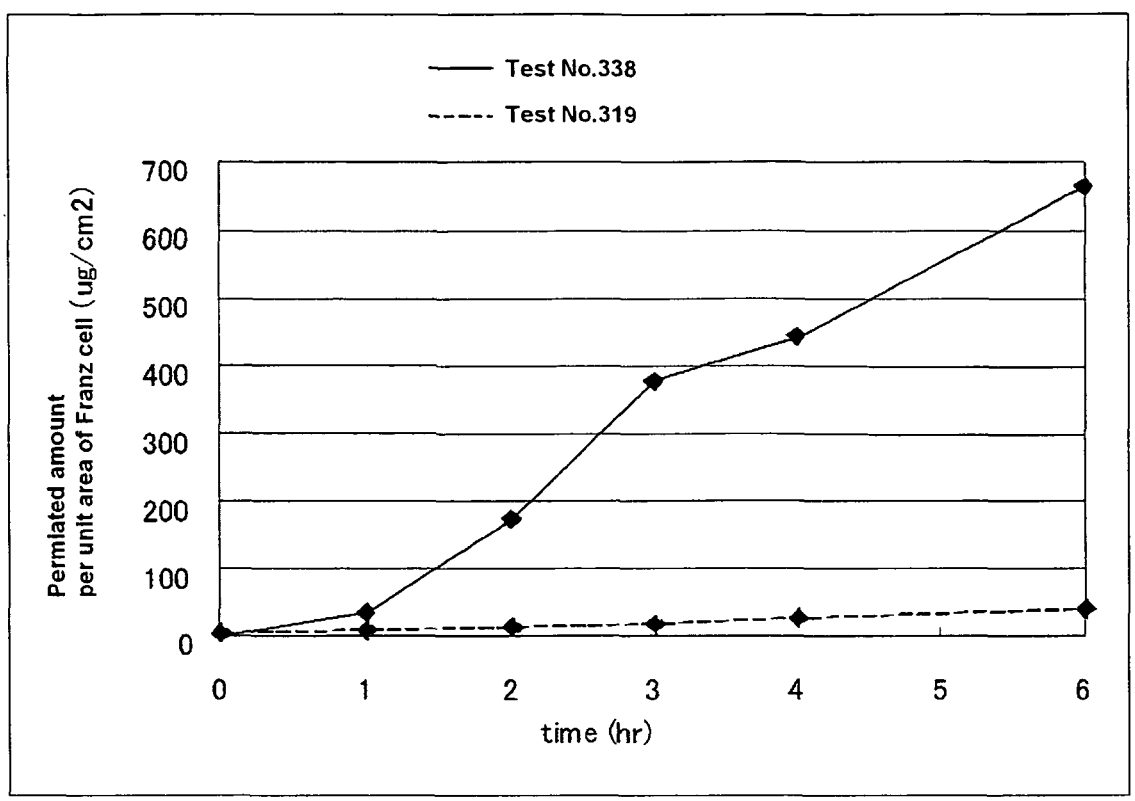
FIG. 1 is a diagram showing the results of a transdermal absorbability evaluation test on an external preparation composition of the present invention.

A first aspect of the present invention relates to an external preparation composition comprising a drug or a salt thereof.

In the present specification, the term "drug" refers to a drug that exhibits acidity ("acidic drug") or a drug that exhibits basicity ("basic drug").

In the present specification, the "acidic drug" is a drug that has carboxylic acid as a functional group and exhibits acidity as a compound. The acidic drug refers to, for example: non-steroidal anti-inflammatory drugs (NSAIDs) such as indomethacin, ketoprofen, ibuprofen, flurbiprofen, diclofenac, etodolac, and loxoprofen; antiallergic drugs such as tranilast, cromoglycic acid, and pemirolast; hypnotic sedatives/anxiolytics such as amobarbital, secobarbital, and phenobarbital; and muscle relaxants such as dantrolene and mibacline. Preferable examples thereof can include indomethacin, flurbiprofen, ketoprofen, etodolac, ibuprofen, loxoprofen, and diclofenac.

In the present invention, the "basic drug" is a drug that has a primary, secondary, or tertiary amine structure as a functional group and exhibits basicity as a compound. Examples of the basic drug can include: local anesthetics such as lidocaine, dibucaine, bupivacaine, procaine, mepivacaine, bupivacaine, and tetracaine; antihistaminics such as diphenhydramine; analgesics such as tramadol; antispasmodics such as eperisone; muscle relaxants such as tolperisone; antitussives such as dextromethorphan; acetylcholinesterase inhibitors such as donepezil; and opioid analgesics such as morphine, codeine, naloxone, and fentanyl. Preferable examples thereof can include lidocaine, tolperisone, bupivacaine, eperisone, tramadol, morphine, and donepezil.

In the present specification, the term "(drug or) salt thereof" refers to a salt prepared from the acidic drug using a base that may be used pharmaceutically in external preparation application or a salt prepared from the basic drug using an acid that may be used pharmaceutically in external preparation application. Examples of the base used here can include: inorganic bases such as alkali metal hydroxide (e.g., sodium hydroxide and potassium hydroxide); and organic bases such as linear or cyclic alkylamine (e.g., n-octylamine, n-hexylamine, piperazine, piperidine, and piperonylamine), hydroxyl group-substituted linear or branched or cyclic alkylamine compounds (e.g., diethanolamine, triethanolamine, diisopropanolamine, triisopropanolamine, 3-dimethylamino-1-propylamine, and N-hydroxyethylpyrrolidine), and aralkylamine (e.g., benzylamine). Examples of the acid used here can include: inorganic acids such as hydrochloric acid and sulfuric acid; and organic acids such as lower alkyl carboxylic acids having 1 to 4 carbon atom(s) (e.g., acetic acid and propionic acid), medium fatty acids having 5 to 10 carbon atoms (e.g., capric acid, octanoic acid, and capric acid), saturated or unsaturated higher fatty acids having 11 to 20 carbon atoms (e.g., lauric acid, myristic acid, palmitic acid, stearic acid, isostearic acid, and oleic acid), and alkylsulfonic acids (e.g., methanesulfonic acid and camphorsulfonic acid).

Furthermore, a salt of the acidic drug and the basic drug may be used.

The content of the drug or the salt thereof can be set to an appropriate amount, if necessary and is preferably 0.5 to 30 w/w %. More preferable examples of the content can include 1 to 20 w/w %.

In the present specification, the term "salt in an ionic liquid form" refers to, among those exemplified as the "salt thereof", a salt that is liquid at room temperature. Examples thereof for the acidic drug can include the followings:

a) Ionic Liquid of Indomethacin:
Dibucaine Salt, Diphenhydramine Salt, Tramadol Salt, eperisone salt, tolperisone salt, dextromethorphan salt, donepezil salt, diethanolamine salt, triethanolamine salt, diisopropanolamine salt, triisopropanolamine salt, and 3-dimethylamino-1-propylamine salt, b) Ionic Liquid of Ketoprofen:
lidocaine salt, dibucaine salt, diphenhydramine salt, tramadol salt, eperisone salt, tolperisone salt, dextromethorphan salt, donepezil salt, diethanolamine salt, triethanolamine salt, diisopropanolamine salt, triisopropanolamine salt, and 3-dimethylamino-1-propylamine salt, c) Ionic Liquid of Flurbiprofen:
lidocaine salt, dibucaine salt, diphenhydramine salt, tramadol salt, eperisone salt, tolperisone salt, dextromethorphan salt, donepezil salt, diethanolamine salt, triethanolamine salt, diisopropanolamine salt, triisopropanolamine salt, and 3-dimethylamino-1-propylamine salt, d) Ionic Liquid of Diclofenac:
dibucaine salt, diphenhydramine salt, eperisone salt, tolperisone salt, dextromethorphan salt, donepezil salt, diethanolamine salt, triethanolamine salt, diisopropanolamine salt, triisopropanolamine salt, and 3-dimethylamino-1-propylamine salt, e) Ionic Liquid of Etodolac:
lidocaine salt, dibucaine salt, diphenhydramine salt, tramadol salt, eperisone salt, tolperisone salt, dextromethorphan salt, donepezil salt, diethanolamine salt, triethanolamine salt, diisopropanolamine salt, triisopropanolamine salt, and 3-dimethylamino-1-propylamine salt, and f) Ionic Liquid of Loxoprofen:
dibucaine salt, dibucaine salt, bupivacaine salt, diphenhydramine salt, tramadol salt, eperisone salt, tolperisone salt, dextromethorphan salt, donepezil salt, diethanolamine salt, triethanolamine salt, diisopropanolamine salt, triisopropanolamine salt, and 3-dimethylamino-1-propylamine salt.

In the present specification, the term "fatty acid-based ionic liquid having 5 to 20 carbon atoms" is obtained through the reaction between fatty acid having 5 to 20 carbon atoms and an organic amine compound and refers to a salt and/or an equilibrium mixture of the fatty acid and the organic amine compound. Examples of the fatty acid having 5 to 20 carbon atoms can include: medium fatty acid having 5 to 10 carbon atoms, such as capric acid, octanoic acid, and capric acid; and saturated or unsaturated higher fatty acid having 11 to 20 carbon atoms, such as lauric acid, myristic acid, palmitic acid, stearic acid, isostearic acid, and oleic acid. Preferable examples thereof can include capric acid, myristic acid, isostearic acid, and oleic acid. Furthermore, a plurality of these acids can be used appropriately to prepare the ionic liquid of the present invention.

The content of the fatty acid-based ionic liquid of the present invention is also related to the amount of the drug or the salt thereof used. Thus, the fatty acid-based ionic liquid is used only in a small amount when the amount of the drug used is small. In the present invention, examples of the content can include 5 to 50 w/w %. More preferable examples of the content can include 5 to 25 w/w %.

In relation to the amount of the drug or the salt thereof used, the fatty acid-based ionic liquid is preferably present in 0.3 to 20-fold molar amount with respect to the amount of the drug or the salt thereof. More preferable examples of the ratio between the amounts can include 3 to 20-fold moles.

In the present specification, the "organic amine compound" is an organic base that forms the fatty acid-based ionic liquid through reaction with the fatty acid having 5 or more carbon atoms. In this context, examples of the organic base can include: substituted or unsubstituted linear or branched alkylamine compounds such as n-octylamine, n-hexylamine, diethanolamine, triethanolamine, diisopropanolamine, triisopropanolamine, 3-dimethylamino-1-propylamine, 2-amino-2-methyl-1-propanol, and 2-amino-2-hydroxymethyl-1,3-propanediol; substituted or unsubstituted cyclic alkylamine compounds such as piperazine, piperidine, piperonylamine, and N-hydroxyethylpyrrolidine; substituted or unsubstituted aralkylamine compounds such as benzylamine; and substituted or unsubstituted heteroaromatic amine compounds such as 1-ethyl-3-methyl-imidazole. A hydroxyl group, a halogen atom (e.g., chlorine or bromine), or a lower alkyl group having 1 to 5 carbon atom(s) that may be substituted by a hydroxyl group or a halogen atom can be used as a substituent. Preferable examples of the organic base can include hydroxyl group-substituted linear or branched alkylamine compounds. More preferable examples thereof can include diethanolamine, triethanolamine, diisopropanolamine, and triisopropanolamine.

In the present specification, the term "organic amine compound having 4 to 12 carbon atoms" refers to, of the organic amine compounds exemplified above, those having 4 to 12 carbon atoms. Preferable examples thereof can include hydroxyl group-substituted linear or branched alkylamine compounds. More preferable examples thereof can include diethanolamine, triethanolamine, diisopropanolamine, and triisopropanolamine, as described above.

The fatty acid-based ionic liquid of the present invention means a salt and/or an equilibrium mixture of the fatty acid and the organic amine compound, as described above. Whether an equimolar reaction product of the fatty acid and the organic amine compound is a salt or an equilibrium mixture in view of IR spectrum is influenced by the difference in pKa between the fatty acid and the organic amine compound. The difference in pKa between the fatty acid and the organic amine compound is preferably approximately around 4 for forming the equimolar salt of the fatty acid and the organic amine compound in view of IR spectrum. When the difference in pKa is approximately around 3, an equilibrium mixture is obtained in which half the amount of the fatty acid used forms a salt.

Figure 2:
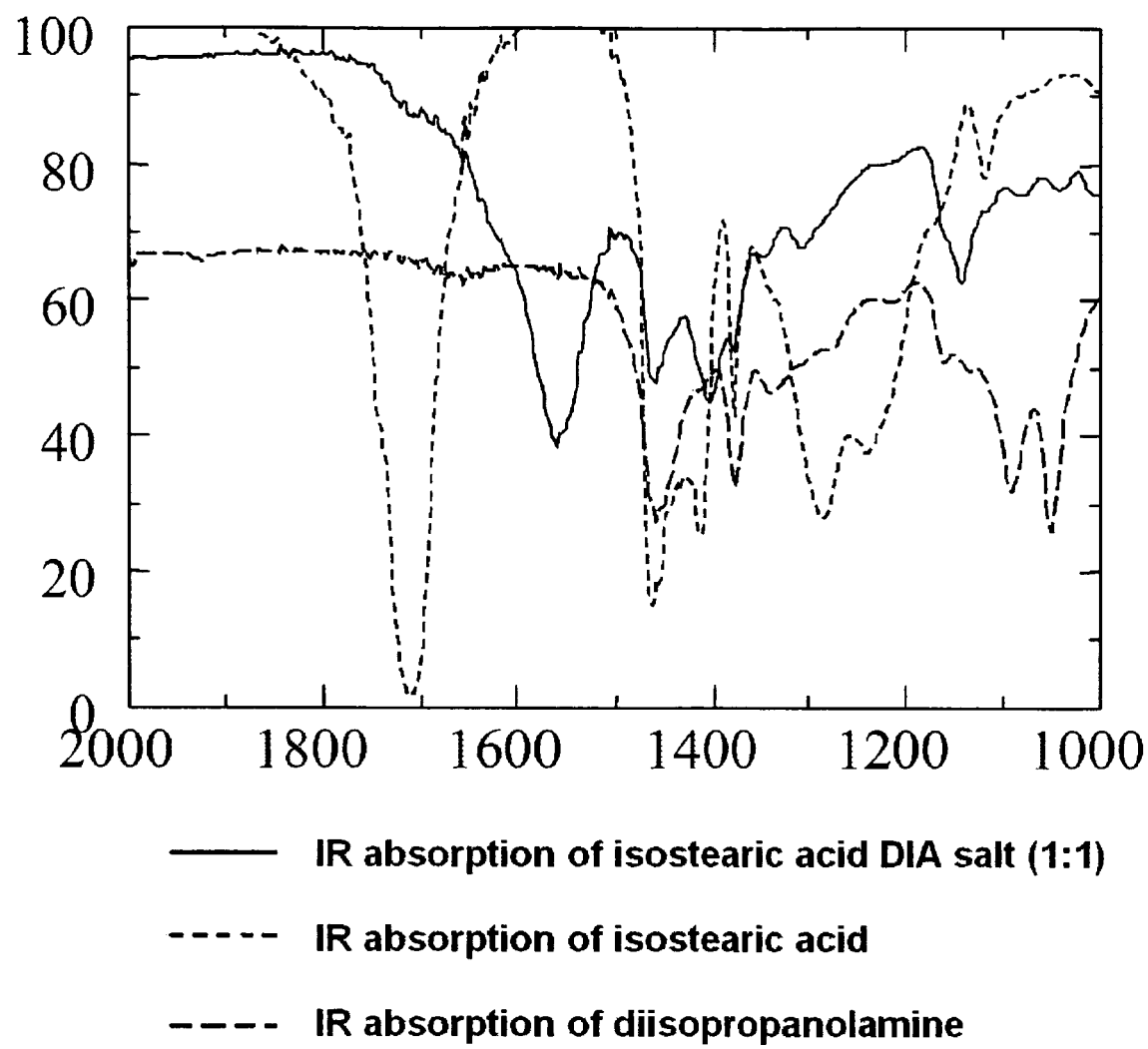
FIG. 2 is a diagram showing the results of measuring the IR spectrum of an isostearic acid-diisopropanolamine equimolar salt.
Figure 3:
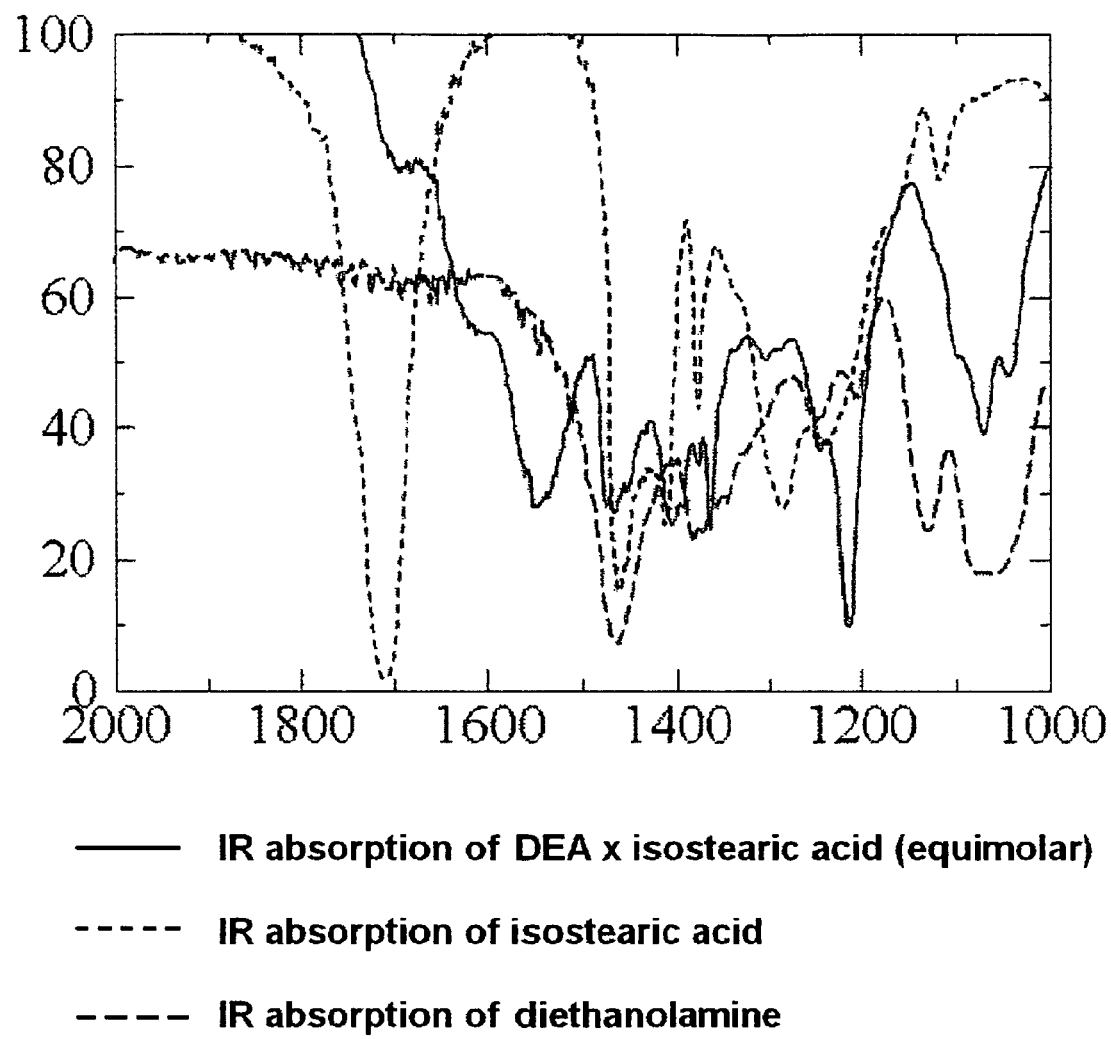
FIG. 3 is a diagram showing the results of measuring the IR spectrum of an isostearic acid-triisopropanolamine equimolar salt.

Since the fatty acid is considered to have an almost constant pKa of approximately 4.5 to 4.9, whether the equimolar reaction product of the fatty acid and the organic amine compound is a salt or an equilibrium mixture in view of IR spectrum is probably determined, mainly depending on the pKa of the organic amine compound. Thus, when an organic amine compound having a pKa of approximately 8.5 or higher (e.g., diisopropanolamine or diethanolamine) is used, a salt is formed as shown in FIG. 2. By contrast, when an organic amine compound having a pKa of approximately 8.5 or lower (e.g., triisopropanolamine or triethanolamine) is used, an equilibrium mixture is formed as shown in FIG. 3.

In the present specification, the term "nonaqueous external preparation composition" refers to an external preparation composition that is not added with water. Specifically, the nonaqueous external preparation composition refers to a composition comprising nonaqueous compounds such as a drug, a fatty acid-based ionic liquid, and an organic solvent. Thus, moisture attached or absorbed to the drug, the fatty acid-based ionic liquid, the organic solvent, or the like is neglected. 又は not considered In general, the acidic drug or the basic drug is often present in an inorganic salt form and is therefore poorly soluble in a nonaqueous organic solvent. Hence, in order to dissolve and formulate their inorganic salts, water-containing formulation is often used, in which their inorganic salts are easily dissolved. However, in case of using the water-containing formulation, a hydrolysis of the drug cannot be avoided. The water-containing formulation largely influences the stability of the drug. Therefore, in case of using nonaqueous pharmaceutical formulation, the formulation can contribute to improvement in the stability of the drug.

In the present invention, by the use of the fatty acid-based ionic liquid having 5 or more carbon atoms, even a drug or a salt thereof poorly soluble in an organic solvent can be solubilized. Therefore, an external preparation having nonaqueous formulation can be prepared easily. As a result, owing to such nonaqueous formulation, the stability of the drug is improved. In addition, the drug further forms a cluster ion composition in the nonaqueous solution and is therefore improved in transdermal absorbability.

Thus, nonaqueous pharmaceutical formulation is preferable for performing pharmaceutical formulation using the fatty acid-based ionic liquid of the present invention.

In the present specification, the "organic solvent" refers to those working to dissolve and solvate a cluster ion composition formed by the drug and the fatty acid-based ionic liquid. Preferably, the organic solvent affects skin surface to improve the transdermal absorbability. For example, the organic solvent working to dissolve and solvate the cluster ion composition is preferably a combination of a proton-donor solvent and a proton-acceptor solvent that can construct solvation based on hydrogen bond.

In the present specification, the "proton-donor solvent" refers to a solvent that tends to donate protons such that hydrogen bond can be constructed. Examples thereof can include organic acids and alcohol solvents. Examples of the alcohol solvents can include: higher alcohols such as benzyl alcohol, lauryl alcohol, myristyl alcohol, cetyl alcohol, stearyl alcohol, cetostearyl alcohol, and 2-octyldodecanol; lower alcohols having 1 to 10 carbon atom(s), such as ethanol, propanol, isopropanol, n-butanol, pentanol, octanol, and dodecanol; and polyhydric alcohols such as ethylene glycol, glycerin, propylene glycol, and 1,3-butylene alcohol. Preferable examples thereof can include ethanol, isopropanol, ethylene glycol, and propylene glycol.

Examples of the organic acids can include: monocarboxylic acids such as lactic acid, propionic acid, capric acid, sorbic acid, salicylic acid, gallic acid, acetic acid, butyric acid, valeric acid, levulinic acid, capric acid, lauric acid, myristic acid, stearic acid, isostearic acid, and oleic acid; dicarboxylic acids such as adipic acid, maleic acid, oxalic acid, malonic acid, succinic acid, glutaric acid, fumaric acid, phthalic acid, isophthalic acid, terephthalic acid, malic acid, and sebacic acid; and tricarboxylic acids such as citric acid. Other pharmaceutically acceptable organic acids may be used. Preferable examples of the organic acids can include acetic acid, oleic acid, levulinic acid, capric acid, myristic acid, and sorbic acid.

In the present specification, the "proton-acceptor solvent" refers to a solvent that tends to accept protons such that hydrogen bond can be constructed. Examples thereof can include: ethers such as THF, butyl ether, and polyethylene glycol methyl ether; ketones such as methyl isobutyl ketone; lower alkyl carboxylic acid esters such as ethyl acetate, propyl acetate, and ethyl butyrate; fatty acid esters such as diethyl sebacate, isopropyl myristate, diisopropyl adipate, myristyl palmitate, stearyl stearate, myristyl myristate, oleic acid triglyceride, ceryl lignocerate, lacceryl cerotate, and lacceryl laccerate; carbonic acid esters such as propylene carbonate; and plant oils such as olive oil and coconut oil. Preferable examples thereof can include: fatty acid esters such as isopropyl myristate and diethyl sebacate; and plant oils such as coconut oil and olive oil.

In the present specification, the term "pyrrolidone derivative" refers to a compound having a pyrrolidone skeleton, such as 2-pyrrolidone, N-methyl-2-pyrrolidone, 5-methyl-2-pyrrolidone, 1,5-dimethyl-2-pyrrolidone, and 1-ethyl-2-pyrrolidone. Preferable examples thereof can include N-methyl-2-pyrrolidone.

In the present specification, examples of the term "organic acid" can include: monocarboxylic acids such as lactic acid, propionic acid, capric acid, sorbic acid, salicylic acid, gallic acid, acetic acid, butyric acid, valeric acid, levulinic acid, capric acid, lauric acid, myristic acid, stearic acid, isostearic acid, and oleic acid; dicarboxylic acids such as adipic acid, maleic acid, oxalic acid, malonic acid, succinic acid, glutaric acid, fumaric acid, phthalic acid, isophthalic acid, terephthalic acid, malic acid, and sebacic acid; and tricarboxylic acids such as citric acid. Other pharmaceutically acceptable organic acids may be used. Preferable examples of the organic acid can include levulinic acid, capric acid, myristic acid, and sorbic acid. The amount of the organic acid used is 1 to 10% by weight, preferably 1 to 5% by weight, of the whole amount.

In the present specification, the term "organic base" refers to the same as the organic amine compounds exemplified above. Those different from the organic amine compounds may be used according to purposes.

—Second Aspect of Present Invention—

A second aspect of the present invention relates to an external preparation containing the composition of the present invention.

In the present specification, the term "base" refers to, among additives other than the active ingredient in a preparation, a basic additive for forming the preparation.

Examples of the base for ointments include Vaseline, liquid paraffin, and Plastibase.

Examples of the base for creams include emulsions containing oil (e.g., squalane, liquid paraffin, Vaseline, lanolin, solid paraffin, and beeswax), water, a surfactant, a humectant, and the like.

Examples of the base for liquid preparations include mixed solutions of alcohols (e.g., isopropanol, ethanol, propylene glycol, and glycerin), fats and oils (e.g., olive oil and soybean oil), and water.

An adhesive is used as a base in patches. The adhesive described here is composed mainly of an elastomer with a tackifier, a softener, a filler, an antioxidant, and the like. Particularly, the softener, the filler, and the antioxidant can be increased or decreased appropriately or omitted, if necessary.

Examples of the elastomer can include: synthetic rubbers such as styrene-isoprene-styrene block (hereinafter, referred to as SIS) copolymers, styrene-butadiene-styrene block copolymers, styrene-ethylene-butadiene rubber-styrene block copolymers, styrene-butadiene rubbers, polyisoprene, polyisobutylene, polybutene, butyl rubbers, and silicon rubbers; acrylic acid resins such as polyacrylic acid methyl ester and polymethacrylic acid methyl ester; and natural rubbers. Preferable examples thereof include those comprising rubber polymers such as styrene-isoprene-styrene block copolymers, styrene-butadiene rubbers, polybutene, polyisoprene, butyl rubbers, and natural rubbers as bases. These elastomers may be used alone or in combination of two or more thereof. Moreover, the resin films may be used alone or as a layer of two or more thereof.

The tackifier refers to alicyclic hydrocarbon resins, polyterpene resins, aliphatic hydrocarbon resins, polystyrene resins, rosin, hydrogenated rosin, and the like. Preferable examples thereof can include alicyclic hydrocarbon resins.

Examples of the softener can include: petroleum softeners such as process oil and low-molecular polybutene; and fatty oil softeners such as castor oil and coconut oil; and purified lanolin.

Examples of the filler can include zinc oxide, titanium oxide, calcium carbonate, and silicic acids.

Examples of the antioxidant can include dibutylhydroxytoluene (hereinafter, referred to as BHT), 4,4-dioxydiphenyl, and EDTA-2Na.

The transdermally absorbable external preparation of the present invention can be applied transdermally as external preparations in various dosage forms. Examples of such dosage forms of external preparations can include liquid preparations, gels, ointments, creams, lotions, liniments, patches, and reservoir-type patches. These dosage forms can be produced by adopting pharmaceutical means generally used.

—Third Aspect of Present Invention—

A third aspect of the present invention relates to use of the fatty acid-based ionic liquid as a transdermal absorption accelerator. The fatty acid-based ionic liquid probably works as a surfactant that achieves the uniformity of an organic solvent separating into two layers and interacts with an acidic drug or a basic drug to form a cluster ion composition in the solution. Furthermore, this cluster ion composition probably works to enhance the skin permeation. As a result, the fatty acid-based ionic liquid serves as a novel transdermal absorption accelerator for an acidic drug or a basic drug.

For enhancing its function as a surfactant, the fatty acid-based ionic liquid preferably contains fatty acid having 10 or more carbon atoms. Examples of such fatty acid can include capric acid, myristic acid, and isostearic acid.

For enhancing the function as a transdermal absorption accelerator, in case of an acidic drug, for example, higher fatty acid (e.g., isostearic acid or oleic acid) and an alkylamine compound having a hydroxyl group are preferably used as fatty acid and an organic amine compound respectively. In case of a free basic drug, the fatty acid is preferably medium fatty acid having around 10 carbon atoms, and the organic amine compound preferably has basicity equal to or weaker than the pKa of the basic drug. Examples of such an organic amine compound can include tertiary amine compounds such as triisopropanolamine and triethanolamine.

—Fourth Aspect of Present Invention—

A fourth aspect of the present invention relates to an equimolar salt of isostearic acid. Since isostearic acid has a pKa of approximately 4.9, an organic amine compound having a pKa of approximately around 8.9 or higher must be used for forming an equimolar salt thereof. Thus, preferable examples of the organic amine compound can include primary and secondary amine compounds. More preferable examples thereof can include diisopropanolamine and diethanolamine.

EXAMPLES

Hereinafter, the present invention will be described more specifically with reference to Examples and Test Example. However, the present invention is not intended to be limited to them by any means.

Example 1

Eternal Preparation Composition Containing Acidic Drug (Indomethacin)

(1) Composition of indomethacin and salt thereof and its transdermal absorbability 100 mg (0.28 mM) of indomethacin is weighed, and in case of preparing a salt thereof, an equimolar amount of an organic base or the like is added thereto. Furthermore, isostearic acid/diisopropanolamine (SDE/PG) was added thereto as a fatty acid-based ionic liquid to adjust the whole amount to 1 g. This sample is directly used. Alternatively, the sample was diluted 4-fold with a solvent to prepare 4 ml of a solution (indomethacin concentration: 2.5%). 100 μl of the solvent-diluted solution was weighed and subjected to a skin permeation test using Franz-cells according to Test Example 1. As shown in Table 1 below, a salt of indomethacin was prepared using an organic base and a basic drug.

In this way, an external preparation composition containing indomethacin or an equimolar salt of indomethacin dissolved in the fatty acid-based ionic liquid was prepared with the composition (numeric values represent w/w %) of Table 1 below and evaluated for its transdermal absorbability. The transdermal absorbability was evaluated based on a cumulative amount permeated 6 hours after the start of the test.

The results are also shown in Table 1 below.

TABLE 1

| Test No. | Evaluated drug (indomethacin content) | #1 | #2 | Solvent |
|---|---|---|---|---|
| Reference Example(26) | indomethacin 2.5% | 3 | 0 | SDE 97.5 |
| 173 | indomethacin 2.5% | 92 | 22.5 | SDE/PG 37.5/37.5 |
| 161 | indomethacin DIA salt 2.5% | 129 | 21.6 | SDE/PG 37.5/37.5 |
| 156 | Indomethacin buprenorphine salt 1.25% | 140 | 22.1 | SDE/PG 37.5/37.5 |
| 158 | Indomethacin eperisone salt 2.5% | 211 | 20.8 | SDE/PG 37.5/37.5 |
| 177 | Indomethacin tolperisone salt 2.5% | 152 | 20.8 | SDE/PG 37.5/37.5 |

[Note]
1 transdermal absorbability (μg/cm$^2$)
2 Fatty acid-based ionic liquid isostearic acid/DIA
DIA: diisopropanolamine
SDE: diethyl sebacate
PG: propylene glycol As shown in these results, indomethacin is poorly transdermally absorbable and exhibits transdermal absorbability as low as approximately 3 μg/cm$^2$ in the absence of the fatty acid-based ionic liquid. However, the dissolution thereof in the ionic liquid improves the transdermal absorbability by approximately 30 times as shown in Test No. 173.

However, Japanese Pharmaceutical Excipients Directory (2007 edition) specifies the upper limits of a fatty acid such as isostearic acid and an alkylamine compound such as diisopropanolamine in use. Thus, the concentration of the fatty acid-based ionic liquid in use must be depressed. However, with increase in the content of the drug used, the amount of the fatty acid-based ionic liquid necessary for dissolution and cluster ion composition formation also increases. In the present invention, the concentration of a fatty acid-based ionic liquid in the external preparation composition was tentatively set to adjust to 25% or lower, and subsequent studies were conducted under this condition.

The composition of the present invention shown in Table 1 above contains acidic and basic substances having the following pKa.

TABLE 2

| Acidic substance | pKa | Basic substance | pKa |
|---|---|---|---|
| Indomethacin | 4.2 | Tramadol | 9.41 |
| Isostearic acid | ca. 4.9 | Eperisone | 8.91 |
| | | Tolperisone | ca. 8.9 (*1) |
| | | Diisopropanolamine | 9.00 |
| | | Buprenorphine | 8.06, 10.54 |

[Note]
(*1) Assumed to be equal to that of eperisone.

In Table 1, the fatty acid-based ionic liquid is present in approximately 7- to 8-fold molar amount with respect to the amount of indomethacin. Moreover, in terms of pKa, the indomethacin salt causes base exchange reaction, when having a pKa lower than or equal to that of the base (diisopropanolamine) in the fatty acid-based ionic liquid. Hence, a cluster ion composition composed mainly of a diisopropanolamine salt is probably formed in the external preparation composition of the present invention of Test No. 156, 161, 177, and 158. The transdermal absorbability of the cluster ion composition would influence the transdermal absorbability of the external preparation composition.

(2) Type of Base in Fatty Acid-Based Ionic Liquid and its Influence on Transdermal Absorbability To evaluate the influence of exchange of the base moiety in the cluster ion composition of indomethacin on the transdermal absorbability, an external preparation composition of indomethacin was prepared with the composition (w/w %) of Table 3 below according to the method of the above paragraph (1). The composition was evaluated for its transdermal absorbability using Franz-cells according to Test Example 1. The transdermal absorbability was evaluated based on a cumulative amount permeated 6 hours after the start of the test.

The results are also shown in Table 3.

TABLE 3

| Test No. | Evaluated drug (indomethacin content) | #1 | #2 | Solvent |
|---|---|---|---|---|
| Reference Example (26) | Indomethacin 2.5% | 3 | 0 | SDE 97.5 |
| 173 | Indomethacin 2.5% | 92 | Isostearic acid DIA 22.5 | SDE/PG 37.5/37.5 |
| 147 | Indomethacin 2.5% | 95 | Isostearic acid DEA 22.5 | SDE/PG 37.5/37.5 |
| 149 | Indomethacin 2.5% | 118 | Isostearic acid TIA 22.5 | SDE/PG 37.5/37.5 |
| 375 | Indomethacin 2.5% | 98 | Isostearic acid TEA 22.5 | SDE/PG 37.5/37.5 |

[Note]
1 transdermal absorbability (µg/cm²)
2 Fatty acid-based ionic liquid
DEA: diethanolamine
TIA: triisopropanolamine
TEA: triethanolamine
The abbreviations DIA, SDE, and PG are as defined above.

According to these results, even if the organic amine compound is changed among secondary amines (diisopropanolamine and diethanolamine) and tertiary amines (triisopropanolamine and triethanolamine) in the isostearic acid-based ionic liquid, this change among these four types of ionic liquids has a little influence on the transdermal absorbability. The transdermal absorbability of indomethacin was almost the same (approximately 100 µg/cm²) among them.

A cluster ion composition composed mainly of a diisopropanolamine salt, a diethanolamine salt, a triisopropanolamine salt, or a triethanolamine salt of indomethacin is formed in the solution. The transdermal absorbability of these cluster ion compositions would influence the transdermal absorbability of the external preparation composition of Table 3. However, it was demonstrated that for the acidic drug indomethacin, the change of the base does not significantly influence the transdermal absorbability.

(3) Type of Acid in Fatty Acid-Based Ionic Liquid and its Influence on Transdermal Absorbability To evaluate the influence of exchange of the acid moiety in the cluster ion composition of indomethacin on the transdermal absorbability, an external preparation composition of indomethacin was prepared with the composition (w/w %) of Table 4 below according to the method of the paragraph (1).

The composition was evaluated for its transdermal absorbability using Franz-cells according to Test Example 1. The transdermal absorbability was evaluated based on a cumulative amount permeated 6 hours after the start of the test.

The results are also shown in Table 4.

TABLE 4

| Test No. | Evaluated drug (indomethacin content) | #1 | #2 | Solvent |
|---|---|---|---|---|
| 173 | Indomethacin 2.5% | 92 | Isostearic acid DIA 22.5 | SDE/PG 37.5/37.5 |
| 376 | Indomethacin 2.5% | 62 | Capric acid DIA 22.5 | SDE/PG 37.5/37.5 |
| 377 | Indomethacin 2.5% | 0.8 (#3) | Levulinic acid DIA 22.5 | SDE/PG 37.5/37.5 |
| 381-2 | Indomethacin 2.5% | 29 | Oleic acid DIA 22.5 | SDE/PG 37.5/37.5 |

[Note]
1 Transdermal absorbability (µg/cm²)
2 Fatty acid-based ionic liquid
The abbreviations DIA, DEA, TIA, SDE, and PG are as defined above.
3 Separated into two layers The SDE/PG solvent tends to separate into two layers and finally, was mixed uniformly at an SDE:PG ratio of approximately 9:1. Moreover, it was confirmed that such a solvent at an SDE:PG ratio of 1:1 became a uniform solution by the addition of a given amount of the fatty acid-based ionic liquid because this ionic liquid acted thereon like a surfactant. Specifically, it was found that a uniform solution was achieved in the presence of 0.2 or more parts of the ionic liquid with respect to 1 part of the solvent at an SDE:PG ratio of 1:1.

The action like a surfactant is strong by use of higher fatty acid such as isostearic acid but not strong by use of capric acid. Levulinic acid was shown to bring about much weaker action. For example, isostearic acid was shown to make a solution at an SDE:PG ratio of 1:1 uniform without separating into two layers as long as the amount of the ionic liquid was 0.16 or more parts.

Thus, change of the acid moiety in the fatty acid-based ionic liquid was evaluated under these conditions for uniformity. In case of using the levulinic acid-based ionic liquid, the solution did not become a uniform solution and separated into two layers.

Indomethacin forms a cluster ion composition of diisopropanolamine salt in the solution. This cluster ion composition contains fatty acid such as isostearic acid, which would largely influence the stability or transdermal absorbability of the cluster ion composition. The results described above support this idea, and the fatty acid-based ionic liquid can contribute to the transdermal absorbability as follows:

TABLE 5

[Tendency of transdermal absorbability of indomethacin]

| | [Isostearate] | > | [Caprate] | > | [Oleate] | > | [Levulinate] |
|---|---|---|---|---|---|---|---|
| transdermal absorbability: | 3 | | 2 | | 1 | | |

(transdermal absorbability brought about by oleic acid-based ionic liquid is defined as 1.)

Since the SDE/PG system is considered to tend to separate into two layers, the use of lower alcohol such as ethanol or isopropanol, rather than PG, can avoid such separation into two layers. Alternatively, the use of an MIP/ethanol system, as shown in the paragraph (5) below, was shown to further improve the transdermal absorbability.

(4) Degree of Salt Formation (Ionic Liquid Form) of Acidic Drug (Indomethacin) and its Influence on Transdermal Absorbability
(Amount of Base Added to Indomethacin and its Effect)

According to the paragraph (1), the amount of diisopropanolamine added with respect to the amount of indomethacin was increased to shift equilibrium reaction in the solution such that a salt of indomethacin was formed. In this way, cluster ion compositions differing in the degree of the ionic liquid form were prepared and studied for their transdermal absorbability. An external preparation composition was prepared according to the composition (w/w %) of Table 6 below and evaluated for its transdermal absorbability according to Test Example 1. The transdermal absorbability was evaluated based on a cumulative amount permeated 6 hours after the start of the test.

The results are shown in Table 6 below.

TABLE 6

| Test No. | Evaluated drug (indomethacin content) | #1 | Ionic liquid isostearic acid DIA | Solvent SDE/PG |
|---|---|---|---|---|
| 173 | Indomethacin 2.5% | 92 | 22.5 | 37.5/37.5 |
| 160 | Indomethacin (2.5%) + DIA 0.5-fold mol | 102 | 22.0 | 37.5/37.5 |
| 161 | Indomethacin (2.5%) + DIA 1.0-fold mol | 129 | 21.6 | 37.5/37.5 |
| 162 | Indomethacin (2.5%) + DIA 2.0-fold mol | 99 | 20.7 | 37.5/37.5 |
| 163 | Indomethacin (2.5%) + DIA 3.0-fold mol | 107 | 19.6 | 37.5/37.5 |
| 164 | Indomethacin (2.5%) + DIA 5.0-fold mol | 73 | 17.5 | 37.5/37.5 |

[Note]
1 Transdermal absorbability ($\mu g/cm^2$)
DIA: diisopropanolamine

In Test No. 173, diisopropanolamine is present in approximately 8-fold molar amount with respect to the amount of indomethacin because of 2.5% indomethacin (2.5 g corresponds to 7 mM) and 22.5% ionic liquid (22.5 g corresponds to 53.9 mM). Since indomethacin and isostearic acid have a pKa of 4.2 and approximately 4.9, respectively, the most part of indomethacin in the solution is probably in a diisopropanolamine salt form.

The transdermal absorbability is increased with increase in the amount of diisopropanolamine added and reaches a peak in the range where diisopropanolamine is added in equimolar to 2-fold molar amount with respect to the amount of indomethacin. It was found that an excess of the base suppressed the transdermal absorption.

According to these results, the transdermal absorbability was approximately around 100 $\mu g/cm^2$) in the range of the amount of amine added up to 3-fold molar amount. This would be affected by the transdermal absorbability of a cluster ion composition (isostearic acid or the like also participates therein) composed mainly of a diisopropanolamine salt of indomethacin formed in the solution.

(5) Influence of Change of Solvent on Transdermal Absorption

The results of the preceding paragraph demonstrated that higher transdermal absorbability was achieved at a higher degree of salt formation (cluster ion composition) of indomethacin. Moreover, the results of the paragraph (3) suggest the possibility of ethanol as an easily uniformly mixed solvent instead of PG. Therefore, this solvent was selected to study the transdermal absorbability of a solvated cluster ion composition. According to the method of the paragraph (1), an external preparation composition was prepared with the composition (w/w %) of Table 7 below and evaluated for its transdermal absorbability according to Test Example 1. The transdermal absorbability was evaluated based on a cumulative amount permeated 6 hours after the start of the test.

The results are shown in Table 7 below.

TABLE 7

| Test No. | Evaluated drug (indomethacin content) | #1 | Fatty acid-based ionic liquid isostearic acid DIA | Solvent |
|---|---|---|---|---|
| 161 | Indomethacin (2.5%) + DIA 1.0-fold mol | 129 | 21.6 | SDE/PG 37.5/37.5 |
| 162 | Indomethacin (2.5%) + DIA 2.0-fold mol | 99 | 20.7 | SDE/PG 37.5/37.5 |
| D522 | Indomethacin (2.5%) + DIA 1.0-fold mol | 2696 | 5 | MIP/ethanol 69.6/21.9 |
| D520 | Indomethacin (2.5%) + DIA 2.0-fold mol | 893 | 5 | MIP/ethanol 69.1/21.5 |
| D521 | Indomethacin (2.5%) + DIA 2.0-fold mol | 768 | 10 | MIP/ethanol 66.6/19 |

[Note]
1 Transdermal absorbability ($\mu g/cm^2$)
The abbreviations DIA, SDE, PG, and MIP are as defined above.

These results show that the transdermal absorbability is improved by 9 times or more by changing the solvent system from an SDE/PG system to an MIP/ethanol system.

Moreover, the amount of the fatty acid-based ionic liquid added can also be decreased because of the uniform solution. In Test No. D522, high transdermal absorbability can be achieved as long as the fatty acid-based ionic liquid is added in approximately 1.7-fold molar amount with respect to the amount of the drug in an ionic liquid form. The larger amount of the fatty acid-based ionic liquid added appears to have no significant influence on the transdermal absorbability as shown in Test No. D521.

(6) Type of Base Used in Salt of Acidic Drug (Indomethacin) and Change in Transdermal Absorption Caused Thereby An equimolar salt (including an ionic liquid) of indomethacin and an organic base is prepared and dissolved in a fatty acid-based ionic liquid to form a cluster ion composition, which is then studied for its transdermal absorbability. According to the method of the paragraph (1), an external preparation composition was prepared with the composition (w/w %) of Table 8 below and evaluated for its transdermal absorbability according to Test Example 1. The transdermal absorbability was evaluated based on a cumulative amount permeated 6 hours after the start of the test.

The results are shown in Table 8 below.

TABLE 8

| Test No. | Evaluated drug (indomethacin content) | #1 | Fatty acid-based ionic liquid isostearic acid DIA | Solvent SDE/PG |
|---|---|---|---|---|
| 161 | DIA salt 2.5% | 129 | 21.6 | 37.5/37.5 |
| 196 | pyrrolidine salt 2.5% | 0 | 21.8 | 37.5/37.5 |
| 204 | piperidine salt 2.5% | 10 | 21.9 | 37.5/37.5 |
| 203 | n-hexylamine salt 2.5% | 6 | 21.6 | 37.5/37.5 |
| 202 | n-octylamine salt 2.5% | 7 | 21.6 | 37.5/37.5 |
| 198 | cyclohexylamine salt 2.5% | 29 | 21.8 | 37.5/37.5 |
| 197 | N-hydroxyethyl-pyrrolidine salt 2.5% | 0 | 21.7 | 37.5/37.5 |
| 200 | piperazine salt 2.5% | 0 | 21.9 | 37.5/37.5 |
| 201 | benzylamine salt 2.5% | 0 | 21.8 | 37.5/37.5 |
| 378 | benzylamine salt 2.5% | 368 | 10 | MIP/ethanol 66.6/19 |

[Note]
1 Transdermal absorbability ($\mu g/cm^2$)
The abbreviations DIA, SDE, PG, and MIP are as defined above.

As shown in these results, all the amine salts do not have favorable transdermal absorbability, compared with the diisopropanolamine salt of Test No. 161. However, the results of Test Nos. 201 and 378 demonstrated that the transdermal absorbability was largely improved, as in the paragraph (5), by changing the solvent from an SDE/PG system to an MIP/ethanol system.

One possible reason why the solvent change largely alters the transdermal absorbability is that the cluster ion composition formed in the solution is solvated, and this solvated cluster ion composition largely influences the transdermal absorbability. Another possible reason is, for example, that the solvent itself affects skin surface to largely alter the permeation of the drug through the skin surface.

The following is suggested as the reason for the low transdermal absorbability of the organic amine salt of indomethacin in the SDE/PG solvent system: acids and organic amine compounds having a pKa shown below are present in the composition of the present invention shown in Table 8 above. Any of the organic amine compounds have basicity higher than that of diisopropanolamine. Thus, base exchange with the base (diisopropanolamine) in the fatty acid-based ionic liquid hardly occurs in the solution. Instead, mainly a cluster ion composition consisting predominantly of each amine salt is probably formed.

TABLE 9

| Acidic substance | pKa | Basic substance | pKa |
|---|---|---|---|
| Indomethacin | 4.2 | Pyrrolidine | 11.40 |
| Isostearic acid | ca.4.9 | Piperidine | 11.12 |
| | | n-Hexylamine | 10.85 |
| | | n-Octylamine | 10.7 (*1) |
| | | Cyclohexylamine | 10.63 |
| | | N-hydroxyethyl-pyrrolidine | 10.32 |
| | | Piperazine | 9.7 |
| | | Benzylamine | 9.43 |
| | | Diisopropanolamine | 9.00 |

[Note]
Values published by The DOW Chemical Company are described as pKa of alkanolamine.
(*1) assumed to be equal to that of n-heptylamine (pKa 10.66).

Thus, the results of Table 8 demonstrated that the cluster ion compositions with various types of amine salts formed in the SDE/PG-based solution were inferior in transdermal absorbability to the cluster ion composition with the diisopropanolamine salt of Test No. 161. The comparison between diisopropanolamine and these various types of organic amine compounds shows that the compounds differ in fat solubility (log P value). This difference in fat solubility is presumably derived from the presence or absence of hydroxyl groups and the number of hydroxyl groups. For example, a compound having one hydroxyl group, such as N-hydroxyethylpyrrolidine produced poor transdermal absorbability, whereas an organic amine compound having 3 hydroxyl groups tended to produce more favorable transdermal absorbability, as shown in the results of Table 3.

In conclusion, the organic amine compound used for forming a salt with an acidic drug preferably has substitution with a plurality of hydroxyl groups. As a result, the organic amine compound with hydroxyl groups can easily participate in hydrogen bond such that an appropriate cluster ion composition is formed in the solution and solvated to produce a transdermally absorbable composition.

Example 2

Transdermally Absorbable Composition Containing Acidic Drug (Flurbiprofen)

According to Example 1(1), an external preparation composition was prepared according to the composition (w/w %) of Table 10 below using flurbiprofen. The composition was measured and evaluated for its transdermal absorbability according to Test Example 1 using Franz-cells. The transdermal absorbability was evaluated based on a cumulative amount permeated 6 hours after the start of the test.

The results are also shown in Table 10 below.

TABLE 10

| Test No. | Evaluated drug (Flurbiprofen content) | #1 | #2 | Solvent |
|---|---|---|---|---|
| Reference Example (23) | Flurbiprofen 2.5% | 8 | 0 | SDE 97.5 |
| 151 | Flurbiprofen 2.5% | 640 | 22.5 | SDE/PG 37.5/37.5 |
| Reference Example (24) | Flurbiprofen lidocaine equimolar salt 2.5% | 8 | 0 | 100 |
| 118 | Flurbiprofen lidocaine equimolar salt 2.5% | 668 | 20.1 | SDE/PG 37.5/37.5 |

TABLE 10-continued

| Test No. | Evaluated drug (Flurbiprofen content) | #1 | #2 | Solvent |
|---|---|---|---|---|
| 122 | Flurbiprofen lidocaine equimolar salt 2.5% | 600 | 20.1 | MIP/PG 37.5/37.5 |

[Note]
1 Transdermal absorbability (μg/cm²)
2 Fatty acid-based ionic liquid isostearic acid/DIA
The abbreviations DIA, SDE, PG, and MIP are as defined above.

Flurbiprofen or its lidocaine salt which forms an ionic liquid is in turn dissolved in a fatty acid-based ionic liquid to form a cluster ion composition. The resulting composition has transdermal absorbability increased up to almost 80 times. Flurbiprofen has a pKa of 3.78 and is an acid stronger than isostearic acid (approximately 4.9). Therefore, a cluster ion composition composed mainly of diisopropanolamine salt of flurbiprofen is probably formed in the solution. Accordingly, Test Nos. 151, 118, and 122 show transdermal absorbability very close to each other.

Moreover, solvent change from SDE to MIP did not largely influence the transdermal absorbability, as shown in Test Nos. 118 and 122.

These results demonstrated that change in the type of a solvent among proton-acceptor solvents had no significant influence thereon. Moreover, change of a proton-donor solvent appears to have stronger influence on the transdermal absorbability, as shown in Test No. D522 of Table 7 or the like.

Example 3

Transdermally Absorbable Composition Containing Acidic Drug (Etodolac)

According to Example 1(1), an external preparation composition was prepared according to the composition (w/w %) of Table 11 below using etodolac. The composition was measured and evaluated for its transdermal absorbability according to Test Example 1 using Franz-cells. The transdermal absorbability was evaluated based on a cumulative amount permeated 6 hours after the start of the test.

The results are also shown in Table 11 below.

TABLE 11

| Test No. | Evaluated drug (Etodolac content) | #1 | #2 | Solvent SDE/PG |
|---|---|---|---|---|
| Reference Example (40) | Etodolac 2.5% (#3) | 16 (#4) | 0 | 50/50 |
| 139 | Etodolac 2.5% | 409 | 22.5 | 37.5/37.5 |
| 140 | Etodolac lidocaine Equimolar salt 2.5% | 437 | 20.5 | 37.5/37.5 |

[Note]
1 Transdermal absorbability (μg/cm²)
2 Ionic liquid isostearic acid/DIA
3 data from mixed system of 5 types of NSAIDs (ketoprofen, flurbiprofen, etodolac, indomethacin, and loxoprofen).
4 Separated into two layers
The abbreviations DIA, SDE, and PG are as defined above.

The etodolac/lidocaine equimolar salt forms an ionic liquid. This ionic liquid is in turn dissolved in a fatty acid-based ionic liquid to form a cluster ion composition. The resulting composition has transdermal absorbability increased up to almost 25 times that of Reference Example 40 free from the fatty acid-based ionic liquid.

Etodolac is lowly acidic with a pKa of 4.5 but has acidity higher than that of isostearic acid (approximately 4.9). Hence, mainly a cluster ion composition consisting predominantly of the diisopropanolamine salt of etodolac is formed in the solution. Therefore, Test Nos. 139 and 140 show almost the same values of transdermal absorbability.

Example 4

Transdermally Absorbable Composition Containing Acidic Drug (Ibuprofen)

According to Example 1(1), an external preparation composition was prepared according to the composition (w/w %) of Table 12 below using ibuprofen. The composition was measured and evaluated for its transdermal absorbability according to Test Example 1 using Franz-cells. The transdermal absorbability was evaluated based on a' cumulative amount permeated 6 hours after the start of the test.

The results are also shown in Table 12 below.

TABLE 12

| Test No. | Evaluated drug (Ibuprofen content) | #1 | #2 | Solvent SDE/PG |
|---|---|---|---|---|
| Reference Example (172) | Ibuprofen 2.5% | 40 (#3) | 0 | 48.7/48.7 |
| 166 | Ibuprofen 2.5% | 520 | 22.5 | 37.5/37.5 |
| 167 | Ibuprofen lidocaine equimolar salt 2.5% | 760 | 19.6 | 37.5/37.5 |

[Note]
1 Transdermal absorbability (μg/cm²)
2 Ionic liquid isostearic acid/DIA
3 Separated into two layers
The abbreviations DIA, SDE, and PG are as defined above.

Ibuprofen exhibits a pKa of 4.25, which is similar to the pKa value of indomethacin. From pKa, it is presumed that a cluster ion composition consisting predominantly of the diisopropanolamine salt of ibuprofen is formed in the solution, as in indomethacin, flurbiprofen, or etodolac described above. Hence, the resulting composition has transdermal absorbability improved to approximately 13 to 19 times that of Reference Example 172 free from the fatty acid-based ionic liquid.

Example 5

Transdermally Absorbable Composition Containing Acidic Drug (Loxoprofen)

According to Example 1(1), an external preparation composition was prepared according to the composition (w/w %) of Table 13 below using ibuprofen. The composition was measured and evaluated for its transdermal absorbability according to Test Example 1 using Franz-cells. The transdermal absorbability was evaluated based on a cumulative amount permeated 6 hours after the start of the test.

The results are also shown in Table 13 below.

TABLE 13

| Test No. | Evaluated drug (Loxoprofen content) | #1 | #2 | Solvent SDE/PG |
|---|---|---|---|---|
| Reference Example (68) | Loxoprofen 2.5% | 40 (#3) | 0 | 48.7/48.7 |

TABLE 13-continued

| Test No. | Evaluated drug (Loxoprofen content) | #1 | #2 | Solvent SDE/PG |
|---|---|---|---|---|
| 154 | Loxoprofen 2.5% | 500 | 22.5 | 37.5/37.5 |
| 155 | Loxoprofen lidocaine equimolar salt 2.5% | 210 | 20.1 | 37.5/37.5 |

[Note]
1 Transdermal absorbability (μg/cm$^2$)
2 Ionic liquid isostearic acid/DIA
3 Separated into two layers
The abbreviations DIA, SDE, and PG are as defined above.

Loxoprofen has a pKa of 4.20, which is almost the same as the value of indomethacin or ibuprofen. Thus, a cluster ion composition consisting predominantly of the diisopropanolamine salt of loxoprofen is probably formed in the solution. Hence, the resulting composition has transdermal absorbability improved to approximately 5 to 13 times that of Reference Example 68 free from the fatty acid-based ionic liquid.

Example 6

Transdermally Absorbable Composition Containing Acidic Drug (Ketoprofen)

According to Example 1(1), an external preparation composition was prepared according to the composition (w/w %) of Table 14 below using ketoprofen. The composition was measured and evaluated for its transdermal absorbability according to Test Example 1 using Franz-cells. The transdermal absorbability was evaluated based on a cumulative amount permeated 6 hours after the start of the test.

The results are also shown in Table 14 below.

TABLE 14

| Test No. | Evaluated drug (ketoprofen content) | #1 | #2 | Solvent SDE/PG |
|---|---|---|---|---|
| Reference Example (40) | Ketoprofen 2.5% (#4) | 50 (#3) | 0 | 50/50 |
| 137 | Ketoprofen 2.5% | 457 | 22.5 | 37.5/37.5 |
| 138 | Ketoprofen lidocaine equimolar salt 2.5% | 134 | 20.2 | 37.5/37.5 |

[Note]
1 Transdermal absorbability (μg/cm$^2$)
2 Ionic liquid
3 Separated into two layers
The abbreviations SDE, PG, and DIA are as defined above.

Ketoprofen has a pKa of 3.90, which is almost the same as the value of flurbiprofen or lidocaine. Thus, a cluster ion composition containing predominantly the diisopropanolamine salt of ketoprofen is probably formed in the solution. Hence, the resulting composition has transdermal absorbability improved to approximately 3 to 9 times that of Reference Example 40 free from the fatty acid-based ionic liquid.

Example 7

Transdermally Absorbable Composition Containing Acidic Drug (Diclofenac)

According to Example 1(1), an external preparation composition was prepared according to the composition (w/w %) of Table 15 below using diclofenac. The composition was measured and evaluated for its transdermal absorbability according to Test Example 1 using Franz-cells. The transdermal absorbability was evaluated based on a cumulative amount permeated 6 hours after the start of the test.

The results are also shown in Table 15 below.

TABLE 15

| Test No. | Evaluated drug (diclofenac content) | #1 | #2 | Solvent |
|---|---|---|---|---|
| Reference Example (7) | Diclofenac 2.5% (#3) | 15 | 0 | SDE 87.5 |
| 135 | Diclofenac 2.5% | 161 | Isostearic acid DIA 47.5 | SDE/PG 25/25 |
| 136 | Diclofenac Lidocaine salt 2.5% | 70 | Isostearic acid DIA 45.5 | SDE/PG 25/25 |
| 306 | Diclofenac Lidocaine equimolar salt 2.5% | 686 | 20.3 Isostearic acid Oleic acid DIA, TIA | SDE/PG/MIP 32.2/10/33 |
| 307 | Diclofenac Lidocaine equimolar salt 2.5% | 921 | 15.9 Isostearic acid DIA + oleic acid DIA (ca. 1:1) | SDE/PG/MIP 32/15/32.6 |
| 299 | Diclofenac Na: 1.0% Lidocaine: 0.74% | 756 | Isostearic acid DIA 15 | SDE/PG/MIP 40.36/5/45 |

[Note]
1 Transdermal absorbability (μg/cm$^2$)
2 Fatty acid-based ionic liquid isostearic acid/DIA
3 data from mixed system containing 2.5% each of five compounds ketoprofen, flurbiprofen, etodolac, diclofenac, and indomethacin.
The abbreviations DIA, TIA, SDE, PG, and MIP are as defined above.
Isostearic acid, oleic acid/DIA, TIA has the composition of isostearic acid (6%), oleic acid (7%), DIA (3.3%), and TIA (4%).

Diclofenac has a pKa of 4.0, while oleic acid and isostearic acid have a pKa of approximately 4.9. Therefore, when diclofenac is dissolved in a fatty acid-based ionic liquid, a cluster ion composition composed mainly of the diisopropanolamine salt of diclofenac is probably formed in the solution. Hence, the resulting composition has transdermal absorbability of diclofenac improved to approximately 5 to 10 times that of Reference Example 7 free from the fatty acid-based ionic liquid.

As shown in Test No. 299, even the diclofenac Na salt is dissolved in the fatty acid-based ionic liquid (isostearic acid/diisopropanolamine) and exhibits high transdermal absorbability. In this case as well, it is presumed that a cluster ion composition of the diisopropanolamine salt or lidocaine salt of diclofenac is formed in the solution, while an Na salt of isostearic acid is also formed to make the solution uniform. Hence, transdermal absorbability similar to that of Test No. 306 or 307 could be exhibited.

Example 8

Transdermally Absorbable Composition Containing Basic Drug (Lidocaine)

(1) Transdermal Absorbability of Lidocaine and its Salt

According to Example 1(1), an external preparation composition was prepared according to the composition (w/w %) of Table 16 below using lidocaine. The composition was measured and evaluated for its transdermal absorbability according to Test Example 1 using Franz-cells. The transdermal absorbability was evaluated based on a cumulative amount permeated 6 hours after the start of the test.

The results are also shown in Table 16 below.

TABLE 16

| Test No. | Evaluated drug (lidocaine content) | #1 | #2 | Solvent |
|---|---|---|---|---|
| Reference Example (11) | Lidocaine 2.5% (#3) | 25 | 0 | SDE 90 |
| 94 | Lidocaine 4.1% (17.4 mM) | 114 | 20.9 (50 mM) | SDE/PG 37.5/37.5 |
| Reference Example (24) | Lidocaine Flurbiprofen equimolar salt 2.5% | 30 | 0 | SDE 95 |
| 118 | Lidocaine Flurbiprofen equimolar salt 2.4% | 130 | 20.1 | SDE/PG 37.5/37.5 |
| 138 | Lidocaine Ketoprofen equimolar salt 2.3% | 70 | 20.2 | SDE/PG 37.5/37.5 |
| 155 | Lidocaine Loxoprofen equimolar salt 2.4% | 100 | 20.1 | SDE/PG 37.5/37.5 |
| 140 | Lidocaine etodolac equimolar salt 2.1% | 90 | 20.5 | SDE/PG 37.5/37.5 |

[Note]
1 Transdermal absorbability ($\mu g/cm^2$)
2 Fatty acid-based ionic liquid isostearic acid/DIA
3 data from mixed system containing 2.5% each of lidocaine, tolperisone, bupivacaine, and eperisone.
The abbreviations DIA, SDE, and PG are as defined above.

Lidocaine or its organic acid salt is dissolved in a fatty acid-based ionic liquid to form a cluster ion composition in the solution. The resulting composition has transdermal absorbability of lidocaine improved in the range of approximately 3 to 5 times the result of Reference Example 11 or 24 free from the fatty acid-based ionic liquid. Specifically, in Test No. 94, lidocaine is probably dissolved in the fatty acid-based ionic liquid to form a cluster ion composition composed mainly of isostearate of lidocaine.

Moreover, as shown in Test Nos. 118, 138, 155, and 140, the transdermal absorbability is improved to a value of approximately around 100 $\mu g/cm^2$ even by use of various types of salts of lidocaine. Things shown below are suggested from these transdermal absorbability data and pKa of various types of acids and bases described in Table 16 above (Table 17 below):

TABLE 17

| Acidic substance | pKa | Basic substance | pKa |
|---|---|---|---|
| Flurbiprofen | 3.78 | Diisopropanolamine | 9.00 |
| Ketoprofen | 3.90 | Lidocaine | 7.86 |
| Loxoprofen | 4.20 | | |
| Etodolac | 4.5 | | |
| Isostearic acid | ca.4.9 | | |

Specifically, in terms of pKa, various types of acids constituting the lidocaine salt causes acid exchange with the fatty acid-based ionic liquid in the solution. For example, when a flurbiprofen salt of lidocaine is used, mainly a diisopropanolamine salt of flurbiprofen is probably formed. Therefore, lidocaine probably forms a cluster ion composition mainly as isostearate salt. As a result, Test Nos. 118, 138, 155, 140 show transdermal absorbability similar to that of Test No. 94. Specifically, this must probably indicate the transdermal absorbability (approximately 100 $\mu g/cm^2$) of isostearate salt of lidocaine.

(2) Type of Fatty Acid-Based Ionic Liquid and its Influence on Transdermal Absorbability It was shown that lidocaine was dissolved in a fatty acid-based ionic liquid to form a new cluster ion composition, which in turn largely contributes to the transdermal absorbability. Therefore, the type of the fatty acid-based ionic liquid was studied as follows:

a) Effect of Acid in Fatty Acid-Based Ionic Liquid

According to Example 1(1), an external preparation composition was prepared according to the composition (w/w %) of Table 18 below using lidocaine. The composition was measured and evaluated for its transdermal absorbability according to Test Example 1 using Franz-cells. The transdermal absorbability was evaluated based on a cumulative amount permeated 6 hours after the start of the test.

The results are also shown in Table 18 below.

TABLE 18

| Test No. | Evaluated drug (lidocaine content) | #1 | #2 | Solvent |
|---|---|---|---|---|
| 94 | Lidocaine 4.1% | 114 | isostearic acid DIA | SDE/PG 37.5/37.5 |
| 93 | Lidocaine 4.1% | 144 | isostearic acid TEA | SDE/PG 37.5/37.5 |
| 92 | Lidocaine 4.1% | 449 | capric acid DIA | SDE/PG 37.5/37.5 |
| 91 | Lidocaine 4.1% | 509 | capric acid TEA | SDE/PG 37.5/37.5 |
| 379 | Lidocaine 4.1% | 250 #3 | Levulic acid DIA | SDE/PG 37.5/37.5 |
| 380 | Lidocaine 4.1% | 146 #3 | Levulic acid TEA | SDE/PG 37.5/37.5 |

[Note]
1 Transdermal absorbability ($\mu g/cm^2$)
2 Fatty acid-based ionic liquid
3 Separated into two layers
The abbreviations DIA, TEA, SDE, and PG are as defined above.

In the study on the effect of the acid in the fatty acid-based ionic liquid, the capric acid system exhibited more excellent transdermal absorbability than that of the isostearic acid system. The levulinic acid-based ionic liquid had weak surfactant effect and failed to suppress the separation of the SDE/PG solvent system into two layers. In terms of the effect of the base in the fatty acid-based ionic liquid, it was shown that tertiary amine having 3 hydroxyl groups (triethanolamine) produces more excellent transdermal absorbability.

The comparison in transdermal absorbability between the cluster ion composition of isostearate and the cluster ion composition of caprate formed in the solution is as shown in Table 19 below. This result is largely different from the tendency of transdermal absorbability of the acidic drug shown in Table 5.

TABLE 19

[Tendency of transdermal absorbability of lidocaine]

| | [Caprate] | > | [Levulinate] | > | [Isostearate] |
|---|---|---|---|---|---|
| Transdermal absorbability | 4 | | 2 | | 1 |

(Relative ratio of transdermal absorbability in fatty acid/DIA-based ionic liquid)

b) Effect of Base in Fatty Acid-Based Ionic Liquid

The base moiety was changed to study its influence on the transdermal absorbability using the capric acid-based ionic liquid, which exhibited high transdermal absorbability.

Measurement was performed in the same way as above, and an external preparation composition was prepared according to the composition (w/w %) of Table 20 below. The composition was measured and evaluated for its transdermal absorbability according to Test Example 1 using Franz-cells.

The transdermal absorbability was evaluated based on a cumulative amount permeated 6 hours after the start of the test.

The results are also shown in Table 20 below.

TABLE 20

| Test No. | Evaluated drug (lidocaine content) | #1 | #2 | Solvent |
|---|---|---|---|---|
| 133 | Lidocaine Capric acid equimolar salt 2.0% | 195 | Capric acid DIA 16.8 | SDE/PG 40/40 |
| 143 | Lidocaine Capric acid equimolar salt 2.0% | 206 | Capric acid DEA 16.8 | SDE/PG 40/40 |
| 146 | Lidocaine Capric acid equimolar salt 2.0% | 190 | capric acid TIA 16.8 | SDE/PG 40/40 |
| 127 | Lidocaine Capric acid equimolar salt 2.0% | 322 | capric acid TEA 16.8 | SDE/PG 40/40 |

[Note]
1 Transdermal absorbability ($\mu g/cm^2$)
2 Fatty acid-based ionic liquid
The abbreviations DIA, TEA, SDE, and PG are as defined above.

The caprate of lidocaine forms, in the solution, different cluster ion compositions depending on the type of the base used in the capric acid-based ionic liquid. Thus, these bases and lidocaine are arranged in the order of pKa as shown in Table 21 below.

|  | (TEA) | < | [Lidocaine] | < | (TIA) | < | (DEA) | < | (DIA) |
|---|---|---|---|---|---|---|---|---|---|
| [Basicity] |  |  |  |  |  |  |  |  |  |
| pKa | 7.77 |  | 7.86 |  | 8.03 |  | 8.88 |  | 9.00 |
| [Transdermal absorbability] |  |  |  |  |  |  |  |  |  |
| ($\mu g/cm^2$) | 322 |  |  |  | 190 |  | 206 |  | 195 |

When bases having basicity stronger than that of lidocaine are used in the capric acid-based ionic liquid, these bases exhibit almost the same transdermal absorbability values of approximately around 200 $\mu g/cm^2$, as shown in Test Nos. 133, 143, and 146. On the other hand, when a base having basicity weaker than that of lidocaine is used, this base exhibits a value of approximately 300 $\mu g/cm^2$, as shown in Test No. 127.

These results demonstrated that a base having basicity stronger than the pKa of the basic drug, in the fatty acid-based ionic liquid did not significantly contribute to the transdermal absorbability. Thus, it was demonstrated that a fatty acid-based ionic liquid comprising, as a base, triethanolamine having basicity weaker than that of lidocaine (pKa 7.86) is preferable for improving the transdermal absorbability of lidocaine.

(3) Influence of Various Types of Lidocaine Salts on Transdermal Absorbability

It was demonstrated that capric acid/triethanolamine was preferable as a fatty acid-based ionic liquid for the transdermal absorption of lidocaine. Thus, various types of equimolar salts of lidocaine were dissolved in this ionic liquid to form a cluster ion composition in the solution. The influence of varying types of organic salts added to lidocaine on the transdermal absorbability was studied.

According to Example 1(1), an external preparation composition was prepared according to the composition (w/w %) of Table 22 below using lidocaine. The composition was measured and evaluated for its transdermal absorbability according to Test Example 1 using Franz-cells. The transdermal absorbability was evaluated based on a cumulative amount permeated 6 hours after the start of the test.

The results are also shown in Table 22 below.

TABLE 22

| Test No. | Evaluated drug (lidocaine content) | #1 | #2 | Solvent |
|---|---|---|---|---|
| 128 | Lidocaine 2.0% | 190 | Capric acid TEA 18 | SDE/PG 40/40 |
| 126 | Lidocaine levulic acid equimolar salt 2.0% | 302 | Capric acid TEA 17 | SDE/PG 40/40 |
| 127 | Lidocaine capric acid equimolar salt 2.0% | 322 | capric acid TEA 16.8 | SDE/PG 40/40 |
| 123 | Lidocaine myristic acid equimolar salt 2.0% | 300 | capric acid TEA 16 | SDE/PG 40/40 |
| 124 | Lidocaine L-tartaric acid equimolar salt 2.0% | 310 | capric acid TEA 16.7 | SDE/PG 40/40 |
| 125 | Lidocaine sorbic acid equimolar salt 2.0% | 341 | capric acid TEA 17 | SDE/PG 40/40 |

[Note]
1 Transdermal absorbability ($\mu g/cm^2$)
2 Fatty acid-based ionic liquid
The abbreviations DIA, TEA, SDE, and PG are as defined above.

As shown in Test No. 128 and Test Nos. 123 to 127, lidocaine and the equimolar organic acid salt of lidocaine differ in transdermal absorbability, when dissolved in the capric acid-based ionic liquid. Specifically, in the comparison between the solution of the organic acid salt of lidocaine and the solution of only lidocaine, the solution of the organic acid salt of lidocaine produced more favorable results of transdermal absorbability.

Moreover, the transdermal absorbability of the organic acid salt of lidocaine dissolved therein exhibited a value of approximately 300 $\mu g/cm^2$, as shown in Test Nos. 123 to 127. This result showed that the type of the organic acid constituting the salt did not significantly influence the transdermal absorbability.

Thus, various types of acids and bases present in the solution are summarized as shown in Table 23 below in terms of pKa.

TABLE 23

| Acidic substance | pKa | Basic substance | pKa |
|---|---|---|---|
| L-tartaric acid | 2.87, 3.97 | Lidocaine | 7.86 |
| Levulinic acid | 4.5 | Triethanolamine | 7.77 |
| Sorbic acid | 4.76 |  |  |
| Capric acid | 4.90 |  |  |
| Myristic acid | ca.4.9 |  |  | lidocaine and triethanolamine have almost the same pKa and capric acid is present in approximately 6- to 7-fold molar amount with respect to the amount of the acid constituting the lidocaine salt. Thus, exchange reaction would occur between lidocaine and triethanolamine in the solution, resulting in a higher concentration at which a cluster ion composition of caprate of lidocaine is formed. Moreover, when the acid constituting the organic acid salt of lidocaine has a pKa higher than that of capric acid (i.e., acidity is strong), base exchange with abundant triethanolamine occurs with a higher probability.

Thus, when capric acid/triethanolamine is used as a fatty acid-based ionic liquid for lidocaine, mainly a cluster ion composition of caprate of lidocaine is probably formed in the solution. Therefore, each of the lidocaine salts could exhibit the transdermal absorbability value of approximately around 300 μg/cm².

(4) Influence of Lidocaine Concentration (Content) on Transdermal Absorbability

In general, the transdermal absorbability of a drug tends to depend on the concentration (content) of the drug. Thus, to confirm whether this fact holds true for lidocaine, compositions having a lidocaine content of 2 to 20 w/w % were prepared and studied for concentration-dependent change in transdermal absorbability, as described below.

According to Example 1(1), an external preparation composition was prepared according to the composition (w/w %) of Table 24 below. The composition was measured and evaluated for its transdermal absorbability according to Test Example 1 using Franz-cells. The transdermal absorbability was evaluated based on a cumulative amount permeated 6 hours after the start of the test.

The results are also shown in Table 24 below.

TABLE 24

| Test No. | Evaluated drug (lidocaine content) | #1 | #2 | Solvent |
|---|---|---|---|---|
| 134 | 2.0% | 260 | Capric acid DIA 18 | SDE/PG 40/40 |
| 92 | Lidocaine 4.1% | 449 | Capric acid DIA 20.9 | SDE/PG 37.5/37.5 |
| 247 | 10.0% + oleic acid 0.23-fold mol | 1050 | Oleic acid DIA 6.2 | MIP/Olive oil 40/41 |
| 279 | 20.0% | 1670 | Oleic acid DIA 10.3 | MIP/Olive oil/SDE/PG 22.7/30/12/5 |

[Note]
1 Transdermal absorbability (μg/cm²)
2 Fatty acid-based ionic liquid
The abbreviations DIA, TEA, SDE, PG, and MIP are as defined above.

As shown in these results, it was demonstrated that higher transdermal absorbability was achieved at a higher lidocaine content (concentration).

At the lidocaine content of 20% (which corresponds to 85.3 mM), 10.3% (which corresponds to 24.8 mM) of the oleic acid-based ionic liquid is present. Thus, the oleic acid-based ionic liquid is present in approximately 0.3-fold molar amount with respect to the amount of lidocaine. However, even such a small amount of the oleic acid-based ionic liquid added produces the effect of improving the transdermal absorbability by approximately twice that produced by Test No. 251 or 252 of Table 25 below.

TABLE 25

| Test No. | Evaluated drug (lidocaine content) | #1 | #2 | Solvent presence or absence of alcoholic solvent |
|---|---|---|---|---|
| 249 | 10% | 200 | 0 | MIP/Olive oil 43/47 |
| 248 | 10% + Oleic acid 0.6-fold mol | 210 | 0 | MIP/Olive oil 42/41 |
| 206 | 15% | 220 | 0 | MIP/SDE 45/40 |

TABLE 25-continued

| Test No. | Evaluated drug (lidocaine content) | #1 | #2 | Solvent presence or absence of alcoholic solvent |
|---|---|---|---|---|
| 248 | 10% | 630 | 0 | MIP/SDE/PG 45/40/5 |
| 251 | 20% + Oleic acid 0.3-fold mol | 850 | 0 | SDE/PG 33/10 |
| 252 | 20% + Oleic acid 0.3-fold mol | 890 | 0 | MIP/SDE/PG 20/13/10 |

[Note]
1 Transdermal absorbability (μg/cm²)
2 Fatty acid-based ionic liquid
The abbreviations DIA, TEA, SDE, PG, and MIP are as defined above.

The results of Table 25 above further demonstrated that the transdermal absorbability of lidocaine was largely altered depending on the presence or absence of the alcohol solvent. Specifically, the presence of the alcohol solvent improves the transdermal absorbability of lidocaine by approximately 3 to 4 times.

These results demonstrated that the coexistence of a proton-donor solvent such as an alcohol solvent with a proton-acceptor solvent such as MIP or SDE further improved the transdermal absorbability of a drug.

Example 9

Transdermally Absorbable Composition Containing Basic Drug (Tramadol)

(1) Transdermal Absorbability of Tramadol

When hydrochloride of tramadol (pKa 9.41) having basicity stronger than that of lidocaine (pKa 7.86) is used, the hydrochloric acid must be removed by use of an organic amine compound having basicity stronger than that of tramadol, as shown in Table 21 above. Therefore, diisopropanolamine having high basicity (pKa 9.00) was selected as an organic amine compound for a fatty acid-based ionic liquid. As a result, a cluster ion composition of tramadol and fatty acid is easily formed. Thus, according to Example 1(1), an external preparation composition was prepared according to the composition (w/w %) of Table 26 below. The composition was measured and evaluated for its transdermal absorbability using Franz-cells. The transdermal absorbability was evaluated based on a cumulative amount permeated 6 hours after the start of the test.

The results are also shown in Table 26 below.

TABLE 26

| Test No. | Evaluated drug (lidocaine content) | #1 | #2 | Solvent |
|---|---|---|---|---|
| 338 | Tramadol HCl 2.0% | 58 #3 | 0 | SDE/PG 48/48 |
| 360 | Tramadol HCl 2.0% | 295 | Capric acid/DIA 22 | SDE/PG 47.5/47.5 |
| 361 | Tramadol HCl 2.0% | 358 | 0 | MIP/ethanol 49/49 |
| 362 | Tramadol HCl 2.0% | 470 | Capric acid/DIA 22 | MIP/ethanol 37.5/37.5 |
| 319 | Tramadol HCl 2.0% + Levulinic acid 1% | 680 | Capric acid/DIA 22 | MIP/ethanol 37.5/37.5 |

[Note]
1 Transdermal absorbability (μg/cm²)
2 Fatty acid-based ionic liquid
3 Separated into two layers
pyrrolidone: N-methyl-2-pyrrolidone
The abbreviations DIA, TEA, SDE, and PG are as defined above.

As shown in Table 26 above, it was demonstrated that the dissolution of tramadol hydrochloride in the fatty acid-based ionic liquid (capric acid/diisopropanolamine salt) further improved the transdermal absorbability.

The acid in the fatty acid-based ionic liquid is present in approximately 8- to 11-fold molar amount with respect to the amount of tramadol. Moreover, in terms of the pKa of the bases present in the solution, tramadol (pKa 9.41) has basicity stronger than that of diisopropanolamine (pKa 9.00).

Thus, from pKa and abundance, it is deduced that tramadol forms a cluster ion composition mainly as caprate in the solution in Test Nos. 360 and 362. It was demonstrated that the MIP/ethanol solvent system produced more preferable transdermal absorbability than the SDE/PG solvent system.

It was also demonstrated that the addition of levulinic acid as an additive further improved the transdermal absorbability.

(2) Influence of Change of Fatty Acid-Based Ionic Liquid on Transdermal Absorbability a) Change of Fatty Acid and its Influence The effect of the type of the fatty acid-based ionic liquid on tramadol hydrochloride was studied. First, the fatty acid moiety in the fatty acid-based ionic liquid was changed to evaluate the transdermal absorbability. Moreover, the solvent system used was, unlike that for lidocaine, an MIP/ethanol system that exhibits no separation into two layers. In the same way as above, an external preparation composition was prepared according to the composition (w/w %) of Table 27 below. The composition was measured and evaluated for its transdermal absorbability according to Test Example 1 using Franz-cells. The transdermal absorbability was evaluated based on a cumulative amount permeated 6 hours after the start of the test.

The results are also shown in Table 27 below.

TABLE 27

| Test No. | Evaluated drug (Tramadol HCl content) | #1 | #2 | Solvent |
|---|---|---|---|---|
| 363 | Tramadol HCl 2.0% | 93 | isostearic acid/DIA 22 | MIP/ethanol 37.5/37.5 |
| 362 | Tramadol HCl 2.0% | 470 | Capric acid/DIA 22 | MIP/ethanol 37.5/37.5 |
| 364 | Tramadol HCl 2.0% | 398 | Levulinic acid/DIA 22 | MIP/ethanol 37.5/37.5 |
| 365 | Tramadol HCl 2.0% | 204 | Oleic acid/DIA 22 | MIP/ethanol 37.5/37.5 |

[Note]
1 Transdermal absorbability ($\mu g/cm^2$)
2 Fatty acid-based ionic liquid
The abbreviations DIA, DEA, TIA, SDE, and MIP are as defined above.

The transdermal absorbability of tramadol largely differs depending on the type of the fatty acid-based ionic liquid used. This difference is presumably based on the difference in transdermal absorbability among cluster ion compositions formed in the solution, as described above. These cluster ion compositions would exhibit the tendency of transdermal absorbability as shown in Table 28 below.

TABLE 28

| [Tendency of transdermal absorbability of tramadol] | | | | | | |
|---|---|---|---|---|---|---|
| | [Caprate] | > | [Levulinate] | > | [Oleate] | > | [Isostearate] |
| transdermal absorbability: | 5 | | 4 | | 2 | | 1 |

(Indicated in relative ratio to isostearate defined as 1)

This tendency of transdermal absorbability is well consistent with that of lidocaine shown in Table 19. This tendency was obtained under the conditions differing both in the basic drug used and in the solvent system used. This suggested that the formation of a capric acid-based cluster ion composition in the solution was preferable for improving the transdermal absorbability of a basic drug.

b) Change of Base and its Influence

To study the effect of the organic amine compound on the capric acid-based cluster ion composition, an external preparation composition was prepared according to the composition (w/w %) of Table 29 below using varying types of fatty acid-based ionic liquids. The composition was measured and evaluated for its transdermal absorbability according to Test Example 1 using Franz-cells. The transdermal absorbability was evaluated based on a cumulative amount permeated 6 hours after the start of the test.

The results are also shown in Table 29 below.

TABLE 29

| Test No. | Evaluated drug (Tramadol HCl content) | #1 | #2 | Solvent |
|---|---|---|---|---|
| 313 | Tramadol HCl 2.0% | 455 | capric acid/DIA 21.5 | MIP/ethanol 40/36.5 |
| 329 | Tramadol HCl 2.0% | 350 | Capric acid/DEA 23 | SDE/Olive oil/ethanol 37.5/17.5/20 |
| 328 | Tramadol HCl 2.0% | 400 | Capric acid/TIA 23 | MIP/Olive oil/ethanol 37.5/17.5/20 |

[Note]
1 Transdermal absorbability ($\mu g/cm^2$)
2 Fatty acid-based ionic liquid
The abbreviations DIA, DEA, TIA, SDE, and MIP are as defined above.

The fatty acid-based ionic liquid is present in approximately 10-fold molar amount with respect to the amount of tramadol hydrochloride. Thus, a cluster ion composition composed mainly of caprate of tramadol is probably formed in each solution. Moreover, the hydrochloric acid moiety in tramadol hydrochloride forms a salt with the organic amine compound in the fatty acid-based ionic liquid. The organic amine compound in the fatty acid-based ionic liquid has basicity weaker than that of tramadol but is present in a larger amount. Therefore, the hydrochloric acid is removed. Thus, mainly the caprate of tramadol is formed in the solution. Hence, all Test Nos. 313, 329, and 328 exhibited a transdermal absorbability value of approximately around 400 $\mu g/cm^2$, demonstrating that the pKa of the organic amine compound had a little influence on the transdermal absorbability as long as the fatty acid-based ionic liquid was present in a large amount with respect to the amount of tramadol.

(3) Influence of Solvent Composition on Transdermal Absorbability

It was demonstrated that capric acid/diisopropanolamine as a fatty acid-based ionic liquid produced particularly favorable transdermal absorbability. Therefore, the cluster ion composition of caprate of tramadol formed in the solution was studied for the influence of change of the solvent system on the transdermal absorbability. In the same way as above, an external preparation composition was prepared according to the composition (w/w %) of Table 30 below. The composition was measured and evaluated for its transdermal absorbability according to Test Example 1 using Franz-cells. The transdermal absorbability was evaluated based on a cumulative amount permeated 6 hours after the start of the test.

The results are also shown in Table 30 below.

TABLE 30

| Test No. | Evaluated drug (Tramadol HCl content) | #1 | #2 | Solvent |
|---|---|---|---|---|
| 362 | Tramadol HCl 2.0% | 470 | capric acid/DIA 22 | MIP/ethanol 37.5/37.5 |
| 313 | Tramadol HCl 2.0% | 455 | capric acid/DIA 21.5 | MIP/olive oil 40/36.5 |
| 342 | Tramadol HCl 2.0% | 400 | capric acid/DIA 22 | MIP/SDE/PG 42/24/10 |
| 352 | Tramadol HCl 2.0% | 350 | capric acid/DIA 22 | MIP/SDE/PG/ethanol 42/17/10/7 |
| 323 | Tramadol HCl 2.0% | 210 | capric acid/DIA 22 | MIP/olive oil/ethanol/pyrrolidone 37.5/10.5/20/8 |
| 320 | Tramadol HCl 2.0% + L.A. 1% | 680 | capric acid/DIA 22 | MIP/olive oil/ethanol 37.5/17.5/20 |
| 368 | Tramadol HCl 2.0% + L.A. 1% | 415 | capric acid/DIA 18 | MIP/olive oil/oleic acid 37.5/32/7.0 |
| 311 | Tramadol HCl 2.0% + L.A. 1% | 379 | capric acid/DIA 21.5 | MIP/olive oil/oleic acid 40/32/3.5 |

[Note]
1 Transdermal absorbability ($\mu g/cm^2$)
2 Fatty acid-based ionic liquid
pyrrolidone: N-methyl-2-pyrrolidone
L.A. Levulinic acid
The abbreviations DIA, DEA, TIA, SDE, and MIP are as defined above.

These results show that the transdermal absorbability varies in the range of 210 to 680 μg/cm² depending on the change of solvent composition. A cluster ion composition composed mainly of caprate of tramadol is formed in the solution and solvated by the solvent coexisting therewith. Thus, one possible reason why the transdermal absorbability varies as shown in Table 30 above is that the solvent used influences the permeation of the drug through skin surface. Another possible reason is that the solvent used alters the property of the cluster ion composition solvated thereby, resulting in change in transdermal absorbability.

For example, as shown in Test No. 320, solvation to some extent appears to be required for improving the transdermal absorbability. It was demonstrated that the addition of lower alkyl alcohol (ethanol) or an organic acid (levulinic acid) was preferable for this purpose.

(4) Effect of Addition of Alcohol Solvent

It was demonstrated that the addition of an alcohol solvent to achieve the promotion of solvation was preferable as a solvent system. Therefore, an alcohol solvent hardly separating into two layers was selected to study its effect.

In the same way as above, an external preparation composition was prepared according to the composition (w/w %) of Table 31 below. The composition was measured and evaluated for its transdermal absorbability according to Test Example 1 using Franz-cells. Particularly, the transdermal absorbability was evaluated based on a cumulative amount permeated after 3 hours into the test.

The results are also shown in Table 31 below.

TABLE 31

| Test No. | Evaluated drug (Tramadol HCl content) | #1 | #2 | Solvent |
|---|---|---|---|---|
| 362 | Tramadol HCl 2.0% | 300 | 22 | MIP/ethanol 37.5/37.5 |
| 353 | Tramadol HCl 2.0% | 255 | 22 | MIP/n-propanl 38/38 |
| 354 | Tramadol HCl 2.0% | 314 | 22 | MIP/isopropanol 38/38 |
| 355 | Tramadol HCl 2.0% | 122 | 22 | MIP/n-octanol 38/38 |

[Note]
1 Transdermal absorbability after 3 hours ($\mu g/cm^2$)
2 Fatty acid-based ionic liquid capric acid/DIA
The abbreviations DIA and MIP are as defined above.

As shown in these results, lower alkyl alcohols such as ethanol and isopropanol exhibited almost the same transdermal absorbability, when used as a proton-donor solvent. However, medium alkyl alcohol such as n-octanol used exhibited half the transdermal absorbability.

(5) Effect of Removing Hydrochloric Acid from Tramadol Hydrochloride

When tramadol hydrochloride is used, hydrochloric acid present in the solution can react with the organic amine compound in the fatty acid-based ionic liquid and partially form, for example, diisopropanolamine hydrochloride. Thus, the removal of hydrochloric acid was studied for simplifying the system. Specifically, hydrochloric acid was removed from tramadol hydrochloride by forming sodium chloride by the addition of an equimolar amount of fatty acid sodium. As a result, a cluster ion composition of a fatty acid salt of tramadol and capric acid can be formed.

Thus, in the same way as above, an external preparation composition was prepared according to the composition (w/w %) of Table 32 below. The composition was measured and evaluated for its transdermal absorbability using Franz-cells. Particularly, the transdermal absorbability was evaluated based on a cumulative amount permeated 4 hours after the start of the test.

The results are also shown in Table 32 below.

TABLE 32

| Test No. | Evaluated drug (Tramadol HCl content) | #1 | #2 | Solvent |
|---|---|---|---|---|
| 9085E | Tramadol HCl: 2.0% Octanoic acid Na: 1.1% | 252 | 8 | MIP/PG 38.9/50.0 |
| 9086I | Tramadol HCl: 2.0% Lauric acid Na: 1.5% | 252 | 8 | MIP/PG 38.9/50.0 |
| 9087M | Tramadol HCl: 2.0% Gluconic acid Na: 1.5% | 173 | 8 | MIP/PG 38.9/50.0 |
| 9088R | Tramadol HCl: 2.0% Myristic acid: 1.7% | 490 | 8 | MIP/PG 38.9/50.0 |

[Note]
1 Transdermal absorbability after 4 hours ($\mu g/cm^2$)
2 Fatty acid-based ionic liquid capric acid/DIA
The abbreviations DIA, MIP, and PG are as defined above.

According to the results of Table 32, the use of fatty acid sodium having 8 to 12 carbon atoms, as in capric acid, exhibited transdermal absorbability of approximately around 250 μg/cm². The use of sodium myristate having 14 carbon atoms improved the transdermal absorbability by approximately twice. However, sodium gluconate having 6 carbon atoms and 5 hydroxyl groups produced unfavorable transdermal absorbability. This would be affected by the transdermal absorbability of the cluster ion composition of tramadol formed in the solution.

Thus, the results of Table 32 above demonstrated that fatty acid having higher fat solubility (fatty acid having a larger number of carbon atoms) in the solvent composition produced more favorable transdermal absorbability of a cluster ion composition of tramadol.

Example 10

Transdermally Absorbable Composition Containing Basic Drug (Morphine)

(1) Transdermal Absorbability of Morphine Salt

Improvement in the transdermal absorbability by a fatty acid-based ionic liquid was studied using morphine as a basic drug. Since morphine has basicity of pKa 8.4, a base having basicity higher than that of morphine as shown in Table 33 below must be selected for the fatty acid-based ionic liquid, based on the results described above, to eliminate hydrochloric acid from morphine.

TABLE 33

| [Basicity] | (TEA) | < | (TIA) | < | (Morphine) | < | (DEA) | < (DIA) |
|---|---|---|---|---|---|---|---|---|
| pKa: | 7.77 | | 8.03 | | 8.4 | | 8.88 | 9.00 |

Thus, diisopropanolamine having a pKa of 9.00 was selected as an organic amine compound for the fatty acid-based ionic liquid.

According to Example 1(1), an external preparation composition was prepared according to the composition (w/w %) of Table 34 below. The composition was measured and evaluated for its transdermal absorbability according to Test Example 1 using Franz-cells. The transdermal absorbability was evaluated based on a cumulative amount permeated 6 hours after the start of the test.

The results are also shown in Table 34 below.

TABLE 34

| Test No. | Evaluated drug | #1 | #2 | Solvent |
|---|---|---|---|---|
| R. Example (374) | Morphine HCl 2.0% | 0 | 0 | PG 98 |
| 388 | Morphine HCl 2.0% | 16 | Capric acid/ DIA 22 | SDE/PG 9.5/66.5 |
| 371-2 | Morphine HCl 2.0% | 850 | Capric acid/ DIA 22 | MIP/ethanol 37.5/37.5 |
| 373-2 | Morphine HCl 2.0% | 278 | Levulinic acid/ DIA 22 | MIP/ethanol 38/38 |
| 369-2 | Morphine HCl 2.0% + L.A. 1% | 1289 | Capric acid/ DIA 22 | MIP/ethanol 37.5/37.5 |
| 370-2 | Morphine HCl 2.0% + L.A. 1% | 626 #3 | Capric acid/ DIA 22 | SDE/olive oil/ ethanol 37.5/17.5/20 |

[Note]
1 Transdermal absorbability after 4 hours (μg/cm$^2$)
2 Fatty acid-based ionic liquid
3 Slightly cloudy
L.A. Levulinic acid
The abbreviations DIA, SDE, PG, and MIP are as defined above.

Morphine hydrochloride is soluble in alcohol solvents but poorly soluble in ester solvents. As shown in, for example, the results of Reference Example 374 and Test Nos. 388 and 371-2, the addition of the fatty acid-based ionic liquid dramatically improved the transdermal absorbability. It was demonstrated that for morphine as well, a capric acid-based ionic liquid as a fatty acid-based ionic liquid produces favorable transdermal absorbability.

Moreover, as shown in Test Nos. 371-2 and 369-2, it was demonstrated that the addition of levulinic acid further improves the transdermal absorbability of a basic drug, as in lidocaine or tramadol.

(2) Influence of Change of Fatty Acid-Based Ionic Liquid on Transdermal Absorbability a) Change of Fatty Acid and its Influence The effect of the type of the fatty acid-based ionic liquid was also studied on morphine hydrochloride. First, the acid moiety in the fatty acid-based ionic liquid was changed to evaluate the transdermal absorbability. Moreover, the solvent system used was, as in that for tramadol, an MIP/ethanol system that exhibits no separation into two layers. In the same way as above, an external preparation composition was prepared according to the composition (w/w %) of Table 35 below. The composition was measured and evaluated for its transdermal absorbability according to Test Example 1 using Franz-cells. The transdermal absorbability was evaluated based on a cumulative amount permeated 6 hours after the start of the test.

The results are also shown in Table 35 below.

TABLE 35

| Test No. | Evaluated drug | #1 | #2 | Solvent |
|---|---|---|---|---|
| 393 | Morphine HCl 2.0% | 153 | Isostearic acid/DIA 22 | MIP/ethanol 37.5/37.5 |
| 371-2 | Morphine HCl 2.0% | 850 | Capric acid/DIA 22 | MIP/ethanol 38/38 |
| 373-2 | Morphine HCl 2.0% | 278 | Levulinic acid/DIA 22 | MIP/ethanol 38/38 |
| 394 | Morphine HCl 2.0% | 524 #3 | Oleic acid/DIA 22 | MIP/ethanol 38/38 |

[Note]
1 Transdermal absorbability (μg/cm$^2$)
2 Fatty acid-based ionic liquid
3 Slightly precipitated
The abbreviations DIA, DEA, TIA, SDE, and MIP are as defined above.

The transdermal absorbability of morphine largely differs depending on the type of the fatty acid-based ionic liquid used and exhibited tendency shown in Table 36 below.

TABLE 36

| [Tendency of transdermal absorbability of morphine] | | | | | | | |
|---|---|---|---|---|---|---|---|
| | [Caprate] | > | [Oleate] | > | [Levulinate] | > | [Isostearate] |
| (Transdermal Absorbability): | 5.5 | | 3 | | 2 | | 1 |

(Indicated in relative ratio to isostearate defined as 1.)

This tendency of transdermal absorbability is well consistent with the tendency of transdermal absorbability of lidocaine (Table 19). However, the above tendency differs from the tendency of transdermal absorbability of tramadol (Table 28) in a different order about oleic acid and levulinic acid. These results suggested that the use of a capric acid-based ionic liquid as a solvent is preferable for improving the transdermal absorbability of a basic drug.

b) Change of Base and its Influence

To study the effect of the organic amine compound in the capric acid-based ionic liquid, an external preparation composition was prepared according to the composition (w/w %) of Table 37 below. The composition was measured and evaluated for its transdermal absorbability according to Test Example 1 using Franz-cells. The transdermal absorbability was evaluated based on a cumulative amount permeated 6 hours after the start of the test.

The results are also shown in Table 37 below.

TABLE 37

| Test No. | Evaluated drug | #1 | #2 | Solvent |
|---|---|---|---|---|
| 387 | Morphine HCl 2.0% | — insoluble | Capric acid/DIA 21.5 | MIP/olive oil 40/36.5 |
| 395 | Morphine HCl 2.0% | 356 | Capric acid/DEA 21.5 | SDE/olive oil/ ethnaol 37.5/17.5/20 |
| 396 | Morphine HCl 2.0% | — #3 | Capric acid/TIA 22 | MIP/olive oil/ ethnaol 37.5/17.5/20 |
| 400 | Morphine HCl 2.0% + L.A. 1% | 664 | Capric acid/DIA 21.5 | MIP/SDE/PG/ethanol 20/20/30/5 |
| 424 | Morphine HCl 2.0% + L.A. 1% | 719 oil | Capric acid/DEA 22 | MIP/SDE/PG/ethanol 20/20/30/5 |

[Note]
1 Transdermal absorbability (μg/cm$^2$)
2 Fatty acid-based ionic liquid
3 Cloudy, insoluble
L.A. Levulinic acid
The abbreviations DIA, DEA, TIA, SDE, and MIP are as defined above.

As shown in Table 37 above, the salt of morphine is highly crystalline and tends to deposit salt crystals in the solution. Thus, a cluster ion composition of morphine can be presumed to be lowly soluble and easily deposited. Therefore, a given amount of an alcohol solvent is probably required. It was demonstrated that the dissolved cluster ion composition, as in Test No. 395, exhibits transdermal absorbability similar to that of tramadol (Test No. 329 in Table 29).

Moreover, it was demonstrated that the transdermal absorbability of these cluster ion compositions of morphine is susceptible to a solvent system or the effect of addition of a transdermal absorption accelerator and is also largely improved by the addition of levulinic acid.

(3) Influence of Solvent Composition on Transdermal Absorbability

Capric acid/diisopropanolamine as a fatty acid-based ionic liquid was shown to produce favorable transdermal absorbability of morphine. Thus, the effect of solvent composition having influence on solubility was studied. In the same way as above, an external preparation composition was prepared according to the composition (w/w %) of Table 38 below. The composition was measured and evaluated for its transdermal absorbability according to Test Example 1 using Franz-cells. The transdermal absorbability was evaluated based on a cumulative amount permeated 6 hours after the start of the test.

The results are also shown in Table 38 below.

TABLE 38

| Test No. | Evaluated drug | #1 | #2 | Solvent |
|---|---|---|---|---|
| 387 | Morphine HCl 2.0% | — insoluble | Capric acid/ DIA 21.5 | MIP/olive oil 40/36.5 |
| 388 | Morphine HCl 2.0% | 16 | Capric acid/ DIA 22 | SDE/PG 9.5/66.5 |
| 371-2 | Morphine HCl 2.0% | 850 | Capric acid/ DIA 22 | MIP/ethnaol 37.5/37.5 |
| 370-2 | Morphine HCl 2.0% + L.A. 1% | 626 #3 | Capric acid/ DIA 22 | MIP/olive oil/ ethanol 37.5/17.5/20 |

[Note]
1 Transdermal absorbability (μg/cm$^2$)
2 Fatty acid-based ionic liquid
3 Slightly Cloudy
L.A. Levulinic acid
The abbreviations DIA, SDE, PG, and MIP are as defined above.

As shown in Table 38 above, precipitates are deposited in the absence of the alcohol solvent. Moreover, it was demonstrated that the addition of lower alkyl alcohol such as ethanol as an alcohol solvent is essential.

It was further demonstrated that the addition of an organic acid such as levulinic acid is preferable, as in lidocaine or tramadol, for improving the transdermal absorbability.

(4) Effect of Addition of Alcohol Solvent

It was demonstrated that the addition of lower alkyl alcohol is preferable as a solvent system and the addition of levulinic acid further produces favorable results, as described above. Therefore, the type of the lower alkyl alcohol was studied. Therefore, in the same way as above, an external preparation composition was prepared according to the composition (w/w %) of Table 39 or 40 below. The composition was measured and evaluated for its transdermal absorbability according to Test Example 1 using Franz-cells. The transdermal absorbability was evaluated based on a cumulative amount permeated 6 hours after the start of the test.

The results are also shown in Table 39 or 40 below.

TABLE 39

| Test No. | Evaluated drug | #1 | #2 | Solvent |
|---|---|---|---|---|
| 369-2 | Morphine HCl 2.0% + L.A. 1% | 1289 | 22 | MIP/ethanol 37.5/37.5 |
| 397 | Morphine HCl 2.0% + L.A. 1% | 455 | 22 | MIP/n-propanol 38/38 |
| 398 | Morphine HCl 2.0% + L.A. 1% | 974 #3 | 22 | MIP/isopropanol 38/38 |
| 399 | Morphine HCl 2.0% + L.A. 1% | 601 | 22 | MIP/SDE/PG/ethanol 25/25/20/5 |
| 400 | Morphine HCl 2.0% + L.A. 1% | 664 | 22 | MIP/SDE/PG/ethanol 20/20/30/5 |
| 436 | Morphine HCl 2.0% + L.A. 1% | 650 #4 | 22 | MIP/SDE/PG/n-propanol 20/20/30/5 |
| 437 | Morphine HCl 2.0% + L.A. 1% | 573 #4 | 22 | MIP/SDE/PG/isopropanol 20/20/30/5 |
| 401 | Morphine HCl 2.0%+ L.A. 1% | 690 | 22 | MIP/SDE/PG/n-propanol 20/20/15/20 |
| 402 | Morphine HCl 2.0% + L.A. 1% | 665 | 22 | MIP/SDE/PG/isopropanol 20/20/15/20 |

TABLE 39-continued

| Test No. | Evaluated drug | #1 | #2 | Solvent |
|---|---|---|---|---|
| 431 | Morphine HCl 2.0% + L.A. 1% | 697 | 22 | MIP/SDE/PG/ethylene glycol 20/20/15/20 |

[Note]
L.A. Levulinic acid
1 Transdermal absorbability ($\mu g/cm^2$)
2 Fatty acid-based ionic liquid capric acid/DIA
3 Slightly precipitated
4 Finely suspended
The abbreviations DIA, MIP, SDE, and PG are as defined above.

As shown in the results of Table 39 above, it was demonstrated that the use of lower alkyl alcohol such as ethanol or isopropanol produces high transdermal absorbability. However, at a lower alkyl alcohol content decreased to around 5%, the effect of the alcohol solvent having influence on the transdermal absorbability was shown to be reduced.

It was also demonstrated that n-propanol, isopropanol, and ethylene glycol at a content increased to 20% do not significantly influence the transdermal absorbability.

The same thing was also found in capric acid/diethanolamine used as a fatty acid-based ionic liquid, as shown in Table 40 below.

TABLE 40

| Test No. | Evaluated drug | #1 | #2 | Solvent |
|---|---|---|---|---|
| 424 | Morphine HCl 2.0% + L.A. 1% | 719 oil | 22 | MIP/SDE/PG/ethanol 20/20/30/5 |
| 434 | Morphine HCl 2.0% + L.A. 1% | 594 #3 | 22 | MIP/SDE/PG/n-propanol 20/20/30/5 |
| 435 | Morphine HCl 2.0% + L.A. 1% | 648 #3 | 22 | MIP/SDE/PG/isopropanol 20/20/30/5 |
| 425 | Morphine HCl 2.0% + L.A. 1% | 730 | 22 | MIP/SDE/PG/n-propanol 20/20/15/20 |
| 426 | Morphine HCl 2.0% + L.A. 1% | 632 #4 | 22 | MIP/SDE/PG/isopropanol 20/20/15/20 |
| 431 | Morphine HCl 2.0% + L.A. 1% | 697 | 22 | MIP/SDE/PG/ethylene glycol 20/20/15/20 |

[Note]
1 Transdermal absorbability ($\mu g/cm^2$)
2 Fatty acid-based ionic liquid capric acid/DEA
3 Finely suspended
4 Slightly precipitated
L.A. Levulinic acid
The abbreviations DIA, MIP, SDE, and PG are as defined above.

These results suggest that diethanolamine has basicity (pKa 8.88) stronger than that of morphine (pKa 8.4) and can therefore remove hydrochloric acid from morphine hydrochloride, as in diisopropanolamine, and the organic amine compound hardly influences the transdermal absorbability as long as the fatty acid-based ionic liquid is present in a large amount. Thus, it was demonstrated that a fatty acid-based ionic liquid prepared from an organic amine compound having basicity stronger than that of morphine produces favorable transdermal absorbability of morphine, as shown in Table 33.

(5) Content of Fatty Acid-Based Ionic Liquid and its Influence On Transdermal Absorbability For improving the transdermal absorbability, its suitable amount of the fatty acid-based ionic liquid was studied with respect to the amount of morphine hydrochloride. Therefore, in the same way as above, an external preparation composition was prepared according to the composition (w/w %) of Table 41 below. The composition was measured and evaluated for its transdermal absorbability according to Test Example 1 using Franz-cells. The transdermal absorbability was evaluated based on a cumulative amount permeated 6 hours after the start of the test.

The results are also shown in Table 41 below.

TABLE 41

| Test No. | Evaluated drug | #1 | #2 | Solvent |
|---|---|---|---|---|
| 400 | Morphine HCl 2.0% + L.A. 1% | 664 | capric acid/DIA 22 | MIP/SDE/PG/ethanol 20/20/30/5 |
| 450 | Morphine HCl 2.0% + L.A. 1% | 505 #3 | capric acid/DIA 8 | MIP/SDE/PG/ethanol 23/23/38/5 |
| 477 | Morphine HCl 2.0% + L.A. 1% | 78 #4 | capric acid/DIA 1 | MIP/SDE/PG/ethanol 26/26/39/5 |
| 424 | Morphine HCl 2.0% + L.A. 1% | 719 oil | capric acid/DEA 22 | MIP/SDE/PG/ethanol 20/20/30/5 |
| 446 | Morphine HCl 2.0% + L.A. 1% | 574 | capric acid/DEA 8 | MIP/SDE/PG/ethanol 23/23/38/5 |
| 475 | Morphine HCl 2.0% + L.A. 1% | 47 #4 | capric acid/DEA 1 | MIP/SDE/PG/ethanol 26/26/39/5 |

[Note]
1 Transdermal absorbability ($\mu g/cm^2$)
2 Fatty acid-based ionic liquid
3 Finely suspended
4 Suspended, precipitated
L.A. Levulinic acid
The abbreviations DIA, MIP, SDE, and PG are as defined above.

The results of Table 41 above demonstrated that the content of a fatty acid-based ionic liquid such as capric acid/diisopropanol is preferably at least 8% (approximately 5-fold molar amount with respect to the amount of morphine) or higher. It was demonstrated that the fatty acid-based ionic liquid at a content as extremely small as 1% (approximately 0.6-fold molar amount with respect to the amount of morphine) forms a few cluster ion compositions of morphine and also produces unfavorable transdermal absorbability.

(6) Effect of Addition of Transdermal Absorption Accelerator

As shown above, levulinic acid is preferable as a transdermal absorption accelerator. To further confirm the effect of other transdermal absorption accelerator (e.g., N-methylpyrrolidone), an external preparation composition was prepared according to the composition (w/w %) of Table 42 below in the same way as above. The composition was measured and evaluated for its transdermal absorbability according to Test Example 1 using Franz-cells. The transdermal absorbability was evaluated based on a cumulative amount permeated 6 hours after the start of the test.

The results are also shown in Table 42 below.

TABLE 42

| Test No. | Evaluated drug | #1 | #2 | Solvent |
|---|---|---|---|---|
| 500 | Morphine HCl 2.0% + NMP 8% | 382 3# | capric acid/DIA 8 | MIP/panasate/isopropanol 32/20/30 |
| 504 | Morphine HCl 2.0% + NMP 8% + L-menthol 2% | 282 #3 | capric acid/DIA 8 | MIP/panasate/isopropanol 30/20/30 |
| 503 | Morphine HCl 2.0% + L.A. 1% + NMP 8% | 741 #3 | capric acid/DIA 8 | MIP/panasate/isopropanol 31/20/30 |
| 505 | Morphine HCl 2.0% + isostearic acid 1% + NMp 8% | 340 #3 | capric acid/DIA 8 | MIP/panasate/isopropanol 31/20/30 |

TABLE 42-continued

| Test No. | Evaluated drug | #1 | #2 | Solvent |
|---|---|---|---|---|
| 506 | Morphine HCl 2.0% + L.A. 1% + isostearic acid 1% + NMP 8% | 836 #3 | capric acid/DIA 8 | MIP/panasate/isopropanol 32/20/30 |

[Note]
1 Transdermal absorbability ($\mu g/cm^2$)
2 Fatty acid-based ionic liquid
3 White precipitate
L.A. Levulinic acid
NMP N-methylpyrrolidone
The abbreviations diiso, MIP, SDE, and PG are as defined above.

As shown in Table 42 above, it was demonstrated that levulinic acid, isostearic acid, and N-methyl-2-pyrrolidone exhibit the effect of accelerating the transdermal absorption. L-menthol was shown to make no significant contribution to the transdermal absorbability. Moreover, as shown in Test No. 506, it was demonstrated that the transdermal absorbability is improved at a increased content of fatty acid such as levulinic acid or isostearic acid.

Thus, among transdermal absorption accelerator generally used, acid or base compounds were preferable, whereas L-menthol was not much preferable. This is probably because the acid or base compounds have larger influence in terms of solvation or the like on the cluster ion composition of morphine formed in the solution.

(7) Effect of Removing Hydrochloric Acid from Morphine Hydrochloride

To eliminate the influence of hydrochloric acid from the cluster ion composition of morphine hydrochloride, the hydrochloric acid was removed from the system by forming sodium chloride through reaction in the solution by the addition of an equimolar amount of sodium caprate. Therefore, in the same way as above, an external preparation composition was prepared according to the composition (w/w %) of Table 43 below. The composition was measured and evaluated for its transdermal absorbability using Franz-cells. The transdermal absorbability was evaluated based on a cumulative amount permeated 6 hours after the start of the test.

The results are also shown in Table 43 below.

TABLE 43

| Test No. | Evaluated drug | #1 | #2 | Solvent |
|---|---|---|---|---|
| 454 | Morphine HCl 2.0% + Na caprate 1.36% (equimolar) | 403 #3 | capric acid/DIA 22 | MIP/SDE/PG/ethanol 20/20/29/5 |
| 457 | Morphine HCl 2.0% + L.A. 1% (equimolar) | 572 #3 | capric acid/DIA 22 | MIP/SDE/PG/ethanol 20/20/29/5 |
| 400 | Morphine HCl 2.0% + L.A. 1% | 664 | capric acid/DIA 22 | MIP/SDE/PG/ethanol 20/20/30/5 |

[Note]
1 Transdermal absorbability ($\mu g/cm^2$)
2 Fatty acid-based ionic liquid
3 Suspended
L.A. Levulinic acid
The abbreviations DIA, MIP, SDE, and PG are as defined above.

As shown in the results of Table 43 above, the comparison between the removal of hydrochloric acid from morphine hydrochloride (Test No. 454) and only the addition of an equimolar amount of levulinic acid demonstrated that the levulinic acid addition without removing hydrochloric acid produces more favorable transdermal absorbability. Furthermore, as seen from the results of Test No. 506 (Table 42) and Test No. 400, the addition of a different type fatty acid from the fatty acid used in the fatty acid-based ionic liquid tends to further improve the transdermal absorbability.

Example 11

Synthesis of Equimolar Salt of Tramadol and Organic Acid (1) Synthesis of 2-ethylhexanoate of Tramadol Tramadol hydrochloride was dissolved in purified water. To this solution, approximately 1.5-fold molar amount of sodium hydroxide was added and dissolved therein. Then, approximately 2-fold volume of ethyl acetate was further added thereto, and the ethyl acetate fraction was collected using a separatory funnel. From this fraction, ethyl acetate was distilled off to obtain tramadol (pKa 9.41) as oil. This tramadol and an equimolar amount of 2-ethylhexanoic acid were added to methanol and uniformly mixed. Then, methanol was distilled off to synthesize 2-ethylhexanoate of tramadol as viscous oil. The obtained viscous oil was directly applied to rock salt plates and measured for its infrared absorption spectrum (FTIR8400S manufactured by Shimadzu Corp.).

In the infrared absorption spectrum (Nujol), the carboxylic acid absorption (1709 cm-1) of the raw material 2-ethylhexanoic acid disappeared, and carboxyl ion absorption (1597 cm-1) newly appeared.

(2) Synthesis of Other Organic Acid Salts

In the same way as in the preceding paragraph, tramadol salts of other organic acids were prepared. Among the obtained tramadol salts, viscous liquids were directly (neat) to rock salt plates and measured, whereas crystals were measured by the Nujol method. These results are also shown in Table 44.

TABLE 44

| Organic acid (added in equimolar amount) | IR absorption of carboxylic acid (cm$^{-1}$) | | Appearance of salt |
|---|---|---|---|
| | Carboxylic acid | Carboxyl ion | |
| (Not added) free tramadol | — | — | oil |
| Isostearic acid | 1703 | 1603 | oil |
| Capric acid | 1708 | 1630 to 1600 (broad) | white crystal ca.65° C. |
| 2-ethylhexanoic acid | 1709 | 1597 | oil |
| Benzoic acid | 1703 | 1595 | white crystal ca.140° C. |
| Butyric acid | 1713 | 1600 | oil |
| Levulinic acid | 1713 | 1600 | oil |
| Lactic acid | 1730 | 1603 | oil |

As a result of IR measurement, free organic carboxylic acid absorption (1700 to 1730 cm-1) disappeared in the equimolar organic carboxylic acid salt of tramadol, while carboxyl anion absorption (1590 to 1630 cm-1) appeared therein.

The decanoate (melting point: approximately 65° C.) and benzoate (melting point: approximately 140° C.) of tramadol were capable of favorably forming crystals. Particularly, the decanoate was poorly soluble in water.

Example 12

Liquid Preparation Containing Equimolar Salt of Tramadol and Organic Acid (1) Liquid Preparation Free from Fatty Acid-Based Ionic Liquid:

Each tramadol salt obtained in Example 11(2) was weighed with the composition (w/w %) of Table 45 below into a sample container, to which 300 mg of liquid paraffin and further a solvent at an isopropyl myristate:medium-chain fatty acid triglyceride (Panasate 810) ratio of 1:1 were subsequently added to adjust the whole amount to 2 g. The mixture was stirred at room temperature for uniformity to prepare a liquid preparation of the tramadol salt. These liquid preparations of the organic acid salt of tramadol were used to conduct a rat skin permeability test according to Test Example 1.

The results are also shown in Table 45.

TABLE 45

| Organic acid salt of tramadol (equimolar salt) | Amount of tramadol salt | Liquid paraffin | IPM:MCT (1:1) | #1 |
|---|---|---|---|---|
| Hydrochloride | 3.0 | 15.0 | 82.0 | 4.5 |
| Isostearate | 5.5 | 15.0 | 79.5 | 3.7 |
| Caprate | 4.4 | 15.0 | 80.6 | 6.4 |
| 2-ethylhexanoate | 3.5 | 15.0 | 81.5 | 12.1 |
| Benzoate | 3.9 | 15.0 | 81.1 | 3.4 |
| Butyrate | 3.5 | 15.0 | 81.5 | 23.8 |
| Levulinate | 3.8 | 15.0 | 81.2 | 6.2 |
| Lactate | 3.5 | 15.0 | 81.5 | 0.2 |

[Note]
IPM: isopropyl myristate
MCT: medium-chain fatty acid triglyceride
1 Rat skin permeability after 6 hours (%) The rat skin permeability was defined as the amount of the medicinal ingredient permeated through the skin after 6 hours and indicated in percentage with respect to the amount of the medicinal ingredient added onto the rat skin.

As shown in Table 45 above, in the liquid preparation free from the fatty acid-based ionic liquid, the butyrate or 2-ethylhexanoate of tramadol was highly transdermally absorbable, and the caprate or the levulinate of tramadol had transdermal absorbability approximately 1.5 times that of the hydrochloride thereof.

(2) Liquid Preparation Containing Fatty Acid-Based Ionic Liquid:

80 mg of tramadol hydrochloride was weighed into a sample container, to which a fatty acid-based ionic liquid and N-methyl-2-pyrrolidone and further each of solvents medium-chain fatty acid triglyceride (Panasate 810), isopropanol, and isopropyl myristate were subsequently added as shown in Table 46 (w/w %) below to adjust the whole amount to 2 g. The mixture was heated and stirred for uniformity to prepare a liquid preparation of tramadol hydrochloride. These liquid preparations containing tramadol hydrochloride were used to conduct a rat skin permeability test according to Test Example 1. The transdermal absorbability was evaluated based on the amount permeated through the skin after 4 hours.

The results are also shown in Table 46.

TABLE 46

| Test No. | tramadol HCl accelerator #3 | #1 | #2 | Solvent |
|---|---|---|---|---|
| 9114V | 4% + NM2P: 6% | 119 | 0 | MIP/panasate/ isopropanol 6/24/60 |
| 9071L | 4% + NM2P: 8% | 1761 | capric acid/DIA 8.0 | MIP/panasate/ isopropanol 30/20/30 |
| 9078I | 4% + NM2P: 8% | 1513 | capric acid/DEA 8.0 | MIP/panasate/ isopropanol 30/20/30 |
| 9083Z | 4% + NM2P: 8% | 785 | levulinic acid/DIA 8.0 | MIP/panasate/ isopropanol 30/20/30 |
| 9079M | 4% + NM2P: 8% | 386 | isostearic acid/DIA 8.0 | MIP/panasate/ isopropanol 32/20/30 |
| 9083Z | 4% + NM2P: 8% | 198 | isostearic acid/DEA 8.0 | |
| 9073W | 4% | 623 | capric acid/DEA 8.0 | MIP/panasate/ isopropanol 32/24/24 |
| 9073X | 4% | 60 | isostearic acid/DEA 8.0 | MIP/panasate/ isopropanol 32/24/24 |

[Note]
NM2P: N-methyl-2-pyrrolidone
1 Transdermal absorbability after 4 hours($\mu g/cm^2$)
2 Fatty acid-based ionic liquid
3 accelerator of transdermal absorption
The abbreviations DIA, DEA, and MIP are as defined above.

As shown in Table 46 above, the use of the fatty acid-based ionic liquid improved the transdermal absorbability in all the cases. The effect of the fatty acid-based ionic liquid on the transdermal absorbability exhibited the same tendency as the results of Table 19 and Table 28. Furthermore, the effect of addition of a lower alkyl alcohol was also large, and the lower alkyl alcohol added in a larger amount was shown to tend to more improve the transdermal absorbability.

Thus, it was found that the transdermal absorbability can be managed by a method which involves decreasing the content of a fatty acid-based ionic liquid and increasing the content of an alcohol solvent or increasing the content of a fatty acid-based ionic liquid and decreasing the content of an alcohol solvent.

Example 13

Preparation of Tape Preparation Containing Tramadol and its Transdermal Absorbability The crystal of tramadol caprate obtained in Example 11(2) was used. The agent was weighed with the composition (w/w %) of Table 47 below, and a tape preparation containing tramadol and a fatty acid-based ionic liquid was prepared by the method for preparing tape preparations known in the art. Specifically, SIS was dissolved by heating. Kaolin, BHT, liquid paraffin, a solvent, and the like were added thereto and mixed. The complete dissolution was confirmed, and a solution of tramadol caprate in a fatty acid-based ionic liquid was then added thereto to obtain a uniform Adhesive base. The obtained Adhesive base was applied to a base to prepare a tape preparation.

To evaluate the transdermal absorbability of the obtained tape preparation, the tape preparation was cut into the shape of Franz-cells and used to conduct a rat skin permeability test according to Test Example 1. The transdermal absorbability of tramadol was evaluated based on the amount permeated through the skin after 6 hours.

The results are also shown in Table 47.

TABLE 47

| | Test No. | | |
|---|---|---|---|
| | E848H | E847F | E841T |
| Tramadol caprate (crystal) | 25.0 | 25.0 | 40.0 |
| Fatty acid-based ionic liquid | isostearic acid/ DIA 7.0 | isostearic acid/ DEA 7.0 | 0 |
| Solvent: isopropyl myristate | 8.0 | 8.0 | Pro carbonate/ MIP 8.0/10.0 |
| Softener: liquid paraffin | 38.7 | 38.7 | 20.0 |
| Elastomer: SIS | 18.0 | 18.0 | 16.0 |
| Excipient: kaolin | 3.0 | 3.0 | 5.5 |
| Antioxidant: BHT | 0.3 | 0.3 | 0.5 |
| Rat skin permeability | 11.6% | 7.3% | 2.5% |

[Note]
MIP: isopropyl myristate
MCT: medium-chain fatty acid triglyceride
The rat skin permeability was defined as a percentage of the amount of the medicinal ingredient permeated through the skin after 6 hours with respect to the amount of the medicinal ingredient added onto the rat skin.

As shown in Table 47 above, the addition of the fatty acid-based ionic liquid also improved the transdermal absorbability of tramadol in the tape preparation, as in the results of the liquid preparation.

Reference Example 1

Preparation of Fatty Acid-Based Ionic Liquid (1) Preparation of Ionic Liquid and Confirmation of Salt Formation by IR Absorption Spectrum 5.0 g each of four types of organic amine compounds shown in Table 48 below was weighed. Each carboxylic acid shown below was weighed in an equimolar amount with respect to the organic amine compound and added thereto. The mixture was heated to 80° C. and stirred. The obtained uniform solutions were sampled and dissolved in or mixed with Nujol, which was then sandwiched between NaCl plates for IR absorption measurement.

Salt formation was confirmed based on an index in which the IR absorption of the carboxylic acid disappears and carboxylic acid ion absorption is foamed. The results are shown in Table 48 below.

TABLE 48

| Equimolar reaction | Octanoic acid C7H15CO2H (pKa = 4.89) | Capric acid C9H19CO2H (pKa = 4.90) | Lauric acid C11H23CO2H (pKa ≈ 4.9) | Isostearic acid C17H35CO2H (pKa ≈ 4.9) |
|---|---|---|---|---|
| Diisopropanolamine (pKa = 9.00) | $CO_2H \rightarrow CO_2^-$ #1 | Same as the left | Same as the left | Same as the left See FIG. 2 |
| Diethanolamine (pKa = 8.88) | $CO_2H \rightarrow CO_2^-$ #1 | Same as the left | Same as the left | Same as the left |
| Triisopropanolamine (pKa = 8.03) | $CO_2H + CO_2^-$ #2 | Same as the left | Same as the left | Same as the left See FIG. 3 |
| Triethanolamine (pKa = 7.77) | $CO_2H + CO_2^-$ #2 | Same as the left | Same as the left | Same as the left |

[Note]
1 Salt formation
2 Equilibrium mixture
$CO_2H \rightarrow CO_2^-$ represents that the IR absorption of the carboxylic acid disappeared and carboxylic acid ion absorption was formed.
$CO_2H + CO_2^-$ represents that absorptions of carboxylic acid and carboxylic acid ions coexist. In this case, the form of an equilibrium mixture in view of IR spectrum is represented.

Furthermore, octanoic acid or lauric acid was reacted with 4-fold molar amount of triethanolamine or triisopropanolamine to shift equilibrium to salt formation. As a result, free carboxylic acid disappeared from the IR absorption spectrum. Thus, the ionic liquid probably requires differing in pKa by approximately around 4, for forming salts.

(2) Preparation of Equimolar Salt of Isostearic Acid 10.68 g of isostearic acid and 5.0 g of diisopropanolamine, or 13.53 g of isostearic acid and 5.0 g of diethanolamine were separately weighed and mixed, and the mixture was heated to approximately 80° C. The obtained colorless viscous solution was measured for its IR spectrum to confirm the disappearance of the carboxyl group. Change in the position of carboxyl group absorption between the equimolar salts of isostearic acid is shown in Table 49 below.

For the IR measurement, isostearic acid and its ionic liquid were partially sampled and dissolved in or mixed with Nujol, which was then applied to rock salt plates and sandwiched therebetween for measurement.

TABLE 49

| | position of IR absorption Characteristic absorption | |
|---|---|---|
| Amine compound | #1 ($cm^{-1}$) | #2 ($cm^{-1}$) |
| Diisopropanolamine | 1710 | 1560 |
| Diethanolamine | 1710 | 1547 |

1 Characteristic absorption of —COOH of isostearic acid
2 Characteristic absorption of —COO⁻ of fatty acid-based ionic liquid (equimolar)

The IR spectrum of the diisopropanolamine salt of isostearic acid (1:1) is shown in FIG. 2. For the purpose of reference, the IR spectrum of a triisopropanolamine salt of isostearic acid (1:1) is shown in FIG. 3.

Reference Example 2

Preparation Containing Indomethacin and Fatty Acid-Based Ionic Liquid

To prepare a tape preparation containing the external preparation composition of the present invention, a composition is prepared which contained 3.4 w/w % indomethacin/diisopropanolamine salt, 7.95 w/w % fatty acid-based ionic liquid (3 w/w % isostearic acid, 2 w/w % oleic acid, 0.35 w/w % capric acid, 2.6 w/w % diisopropanolamine), 4.4 w/w % solvent (2 w/w % MIP, 2 w/w % SDE, 0.4 w/w % stearyl alcohol), 18.8 w/w % liquid paraffin, 1 w/w % BHT, 44 w/w % Arkon p-100, and 20.45 w/w % SIS5250p. This composition is used to prepare a tape preparation containing the indomethacin salt and the fatty acid-based ionic liquid.

Test Example 1

Transdermal Absorbability Evaluation Test Using Franz-Cells

Six-week-old male Wister rats were used. On the day before the test; the abdomen was shaved using an electrical shaver, and the abdominal skin was excised after euthanasia with ether. According to circumstances, commercially available frozen products of male Wister rat skin were used. These abdominal skins were respectively sandwiched between vertical diffusion cells (effective diffusion area: 1 cm²). Each composition of Examples and Reference Example described in Table 1 was applied to the stratum corneum side, and saline was applied to the dermis side. The experiment temperature was set to 32° C., and 300 μL of the saline were sampled on 2, 4, and 6 hours into the experiment and measured by HPLC for the concentration of the drug eluted through the skin to measure the cumulative amount of the drug permeated on these time points.

Results obtained using, for example, tramadol hydrochloride, are shown. The results obtained without the fatty acid-based ionic liquid (Test No. 338) and the results obtained using the fatty acid-based ionic liquid (Test No. 319) are shown in FIG. 1 as typical examples.

Industrial Applicability

An external preparation of the present invention is characterized by that by using a fatty acid-based ionic liquid, an acidic medicinal ingredient or a basic medicinal ingredient is dissolved in it to form a cluster ion composition. By the selection of a suitable solvent composition and adhesive base composition for this cluster ion composition, liquid preparations, ointments, tape preparations, and the like having favorable transdermal absorbability could be prepared. It was shown that the by use of the fatty acid-based ionic liquid of the present invention, external preparations can be prepared even for a medicinal ingredient whose administration route has usually been limited to oral administration due to its poor transdermal absorbability. As a result, new uses for a medicinal ingredient difficult to orally administer due to problems such as harmful side effects or metabolism could be developed by applying the external preparation of the present invention thereto.

The invention claimed is:

1. A nonaqueous external preparation composition comprising a drug or a salt thereof dissolved in a fatty acid-based ionic liquid having 5 to 20 carbon atoms,
  wherein the drug is an acidic drug;
  the fatty acid-based ionic liquid is an equimolar salt(s) of one or more fatty acid(s) and one or more organic amine compound(s) and is obtained from a fatty acid having 5 to 20 carbon atoms and an organic amine compound having 4 to 12 carbon atoms;
  the fatty acid(s) is one or more selected from capric acid, isostearic acid, and oleic acid; and
  the organic amine compound(s) is one or more selected from diethanolamine, triethanolamine, diisopropanolamine, and triisopropanolamine.

2. The external preparation composition according to claim 1, further comprising an organic acid, in addition to the fatty acid-based ionic liquid.

3. The external preparation composition according to claim 2, wherein the organic acid is a fatty acid having 5 to 20 carbon atoms.

4. The external preparation composition according to claim 1, wherein the acidic drug is a medicinal ingredient having a carboxyl group.

5. The external preparation composition according to claim 4, wherein the acidic drug is NSAID.

6. The external preparation composition according to claim 5, wherein the NSAID is selected from indomethacin, flurbiprofen, etodolac, ibuprofen, loxoprofen, ketoprofen, and diclofenac.

7. A nonaqueous tape preparation comprising an external preparation composition according to claim 1 formulated with a styrene-isoprene-styrene copolymer as a patch base.

8. A nonaqueous ointment preparation comprising an external preparation composition according to claim 1 formulated with Plastibase as an ointment base.

9. A transdermal absorption accelerator for an acidic drug or a salt thereof, comprising, as an active ingredient, a fatty-acid based ionic liquid,
  wherein the fatty acid-based ionic liquid is an equimolar salt(s) of one or more fatty acid(s) and one or more organic amine compound(s), the fatty acid(s) being selected from capric acid, isostearic acid, and oleic acid and the organic amine compound(s) being selected from diethanolamine, triethanolamine, diisopropanolamine, and triisopropanolamine.

10. The transdermal absorption accelerator according to claim 9, wherein the fatty acid-based ionic liquid is an isostearic acid-based ionic liquid.

11. The transdermal absorption accelerator according to claim 9, wherein the organic amine compound forming the fatty acid-based ionic liquid is diisopropanolamine or diethanolamine.

12. A fatty acid-based ionic liquid which is an equimolar salt of isostearic acid and diisopropanolamine or diethanolamine.

* * * * *